(12) United States Patent
Qin et al.

(10) Patent No.: US 9,809,827 B2
(45) Date of Patent: Nov. 7, 2017

(54) TRANSGENIC MAIZE

(71) Applicant: Institute of Botany, The Chinese Academy of Science, Beijing (CN)

(72) Inventors: Feng Qin, Beijing (CN); Shengxue Liu, Beijing (CN); Xianglan Wang, Beijing (CN); Hongwei Wang, Beijing (CN)

(73) Assignee: Institute of Botany, The Chinese Academy of Sciences, Veijing (CN)

( * ) Notice: Subject to any disclaimer, the term of this patent is extended or adjusted under 35 U.S.C. 154(b) by 26 days.

(21) Appl. No.: 14/905,852

(22) PCT Filed: Jul. 18, 2014

(86) PCT No.: PCT/CN2014/082541
§ 371 (c)(1),
(2) Date: Jan. 18, 2016

(87) PCT Pub. No.: WO2015/007240
PCT Pub. Date: Jan. 22, 2015

(65) Prior Publication Data
US 2016/0160230 A1    Jun. 9, 2016

(30) Foreign Application Priority Data
Jul. 18, 2013 (CN) .......................... 2013 1 0303107

(51) Int. Cl.
*C12N 15/82* (2006.01)
*C07K 14/415* (2006.01)

(52) U.S. Cl.
CPC ........ *C12N 15/8273* (2013.01); *C07K 14/415* (2013.01); *C12N 15/8237* (2013.01)

(58) Field of Classification Search
None
See application file for complete search history.

(56) References Cited

U.S. PATENT DOCUMENTS

| 7,569,389 B2 | 8/2009 | Feldmann et al. |
| 7,750,207 B2 | 7/2010 | Wu et al. |
| 2007/0209085 A1 | 9/2007 | Wu et al. |
| 2012/0017338 A1* | 1/2012 | Wu ...................... C07K 14/415 800/300 |

FOREIGN PATENT DOCUMENTS

WO    2010121316    10/2010

OTHER PUBLICATIONS

Patent Cooperation Treaty, "International Search Report" issued in connection to International Application No. PCT/CN2014/082541, dated Dec. 19, 2014, 5 pgs. Dec. 19, 2014.

* cited by examiner

*Primary Examiner* — Brent Page
(74) *Attorney, Agent, or Firm* — McKee, Voorhees & Sease, PLC

(57) ABSTRACT

The present invention provides a method of producing transgenic plants which are drought resistant, plants obtainable by the method and uses thereof.

37 Claims, 5 Drawing Sheets

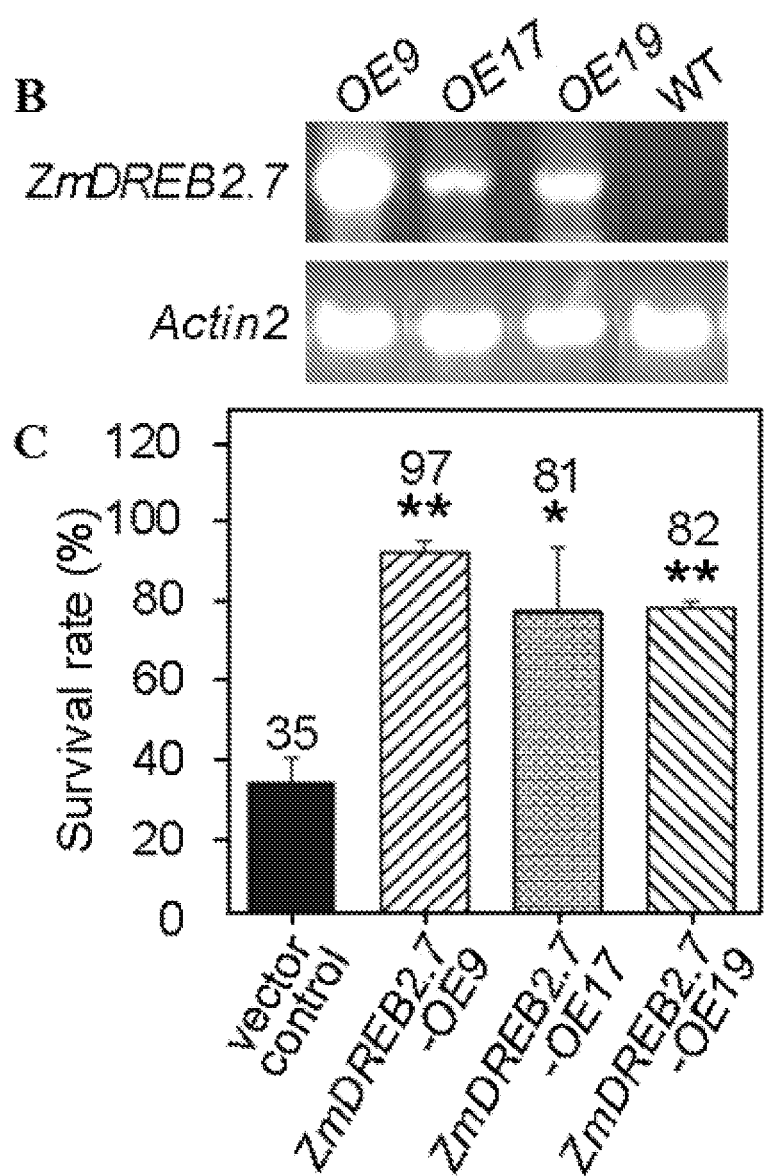
FIG. 3(B)-(C)

TRANSGENIC MAIZE

FIELD OF THE INVENTION

The invention relates to plants that are drought resistant and related methods and uses.

BACKGROUND OF THE INVENTION

Introduction

Maize (*Zea mays* L.) is one of the most planted crops world-wide and has tremendous value for providing food, forage, pharmaceuticals, and other industrial products. Its productivity is frequently hampered by water scarcity and therefore, improved drought tolerance is an important goal in many breeding programs. Considerable research has been conducted to better understand the genetic and molecular basis for drought tolerance in plants with the idea that this research will provide information that will greatly increase the efficiency of traditional breeding programs to select for drought tolerance through the use of molecular markers. Alternatively, this research can be used to identify specific genes that can be used to improve drought tolerance in maize and other crop species using transformation technologies.

Abiotic stress research in *Arabidopsis* has revealed two major signaling pathways, one ABA-dependent and one ABA-independent, that control stress-inducible gene expression, "ABA" here referring to abscisic acid. DREBs/CBFs (Dehydration Responsive Element Binding proteins/C-repeat Binding Factors, hereafter referred as DREBs) are thought to be the major transcription factors (TFs) that control stress-inducible gene expression in the ABA-independent pathway [1]. DREB TFs, belonging to the APETALA2/Ethylene-Responsive Factor (AP2/ERF) super-family of TFs, are able to bind a Dehydration Responsive Element (DRE, core motif: A/GCCGAC, also known as a C-repeat and low-temperature-responsive element [2]-[4], in the promoter region of many drought and/or cold stress-inducible genes. They were first identified using a yeast one-hybrid system to screening for the trans-factors of the DRE element identified in a set of drought and cold-inducible gene promoters [5], [6]. There are two groups of DREB genes in the *Arabidopsis* genome (DREB1s and DREB2s) that are composed of six and eight members, respectively [7]. Ectopic or selective expression of DREB1A/CBF3 can significantly enhance plant tolerance to multiple abiotic stresses, including drought, freezing and high salinity [6], [8]. Over-production of a constitutive active form of DREB2A (DREB2A-CA) protein conferred significant both drought and heat tolerance in transgenic plants [9], [10]. Thus, distinct from DREB1, post-translational modification of the DREB2A protein was demonstrated to finely modulate its abundance and activity [11].

In plants, the DREB gene family consists of multiple genes. Studies in species such as rice, tomato, soybean, wheat, barley and maize, suggest that DREB genes play a central role in plant stress response [15], [16]. Although DREB genes are primarily involved in the regulation of water-stress-related gene expression, other functions have been noted for specific DREB genes. For example, DREB1D/CBF4 plays a role in plant drought stress tolerance which is in contrast to the homologous DREB1A/CBF3 gene that functions in cold response [12]. DREB1C/CBF2 has been characterized as a negative, but not a positive, regulator of plant cold stress response by tightly controlling DREB1A/CBF3 and DREB1B/CBF1 expression [13]. DREB2C has been reported to play a role in heat rather than drought tolerance [14]. Thus it is not possible to predict what effect any particular DREB gene or allelic form of such gene will have in a plant, when selected for by breeding or introduced ectopically. The functional divergence of different DREB genes has proven to be an attractive and challenging topic of research.

Overexpression of the *Arabidopsis* DREB2A gene does not result in a notable drought tolerant phenotype in transgenics, which is most likely a result of the instability of the ectopic expressed protein in plant cells [9], [11] In maize, two DREB genes (ZmDREB1A and ZmDREB2A) belonging to the DREB1 and DREB2 subgroups, respectively, were cloned and demonstrated to be upregulated in response to plant water stress [17], [18]. However, previous reports indicate that transgenic plants constitutively overexpressing DREB2A-CA or ZmDREB2.1/2A gene exhibited a dwarf phenotype in addition to enhanced drought tolerance [9], [18] which impacts negatively on yield. It was also found that, distinct from *Arabidopsis* DREB2A, ZmDREB2A gene expression in response to abiotic stress was regulated via an alternative splicing mechanism and that the expressed protein could directly activate downstream gene expression [18]. Similar findings in rice, wheat and barley, indicate the presence of a mechanism that finely modulates the activity of stress-inducible TF genes and suggest that the molecular mechanism is different in monocot and dicot plants [19]-[21]. To the best of the inventors' knowledge, prior to the invention, other homologous DREB genes in maize have not been identified and characterized.

The inventors have identified a DREB gene in maize which can be expressed in plants to yield transgenic plants that are drought resistant and do not show dwarfism. The invention is aimed at providing a transgenic plant that shows drought resistance and related methods and uses.

SUMMARY OF THE INVENTION

The inventors have identified and characterised a DREB transcription factor gene in maize, ZmDREB2.7 In vitro protein-DNA binding assay demonstrated that ZmDREB2.7 protein could specifically interact with the target DNA sequences. The inventors have also generated transgenic *Arabidopsis* overexpressing ZmDREB2.7 which displayed enhanced tolerance to drought stress compared to control plants that did not overexpress ZmDREB2.7. These plants did not show growth penalties. The identification of ZmDREB2.7 and its role in conferring drought resistance is of significant value as this makes it possible to generate transgenic drought resistant plants which are important in agriculture.

Therefore, in a first aspect, the invention relates to a transgenic plant or part thereof expressing a nucleic acid construct comprising a nucleic acid as defined in SEQ ID NO. 1 or 2 or a functional variant thereof.

The invention also relates to a product derived from a plant as defined in a preceding claim of from a part thereof.

In another aspect, the invention relates to a vector comprising a nucleic acid as defined in SEQ ID NO. 1 or 2 or a functional variant thereof.

In another aspect, the invention relates to a host cell comprising a as described above.

In another aspect, the invention relates to a use of a nucleic acid as defined in SEQ ID NO. 1 or 2 or a functional variant or a vector as described above in conferring drought resistance.

In another aspect, the invention relates to a use of a nucleic acid as defined in SEQ ID NO. 1 or 2 or a functional variant or a vector as described above in increasing yield/growth of a plant under drought stress conditions.

In another aspect, the invention relates to a method for increasing drought resistance of a plant said method comprising introducing and expressing in said plant a nucleic acid construct comprising nucleic acid as defined in SEQ ID NO. 1 or 2 or a functional variant thereof.

In another aspect, the invention relates to a method for increasing yield of a plant under drought or water deficit conditions said method comprising introducing and expressing in said plant a nucleic acid construct comprising nucleic acid as defined in SEQ ID NO. 1 or 2 or a functional variant thereof.

The invention is further described in the following non-limiting figures.

The phylogenetic tree was constructed based on the sequence alignments of sixty-six, full-length DREB genes from four species. The gene codes and names are illustrated for maize, rice, sorghum and *Arabidopsis*. The gene names used for AtDREBs, OsDREB1s and OsDREB2s were according to Sakuma et al., 2002 [7], Mao et al., 2012 [22], and Matsukura et al., 2010 [19]. Genes contained within a blue-box were considered to be direct orthologous genes across species. Bootstrap values from 1,000 replicates were indicated at each node and the scale represents branch lengths.

Figure 2A:
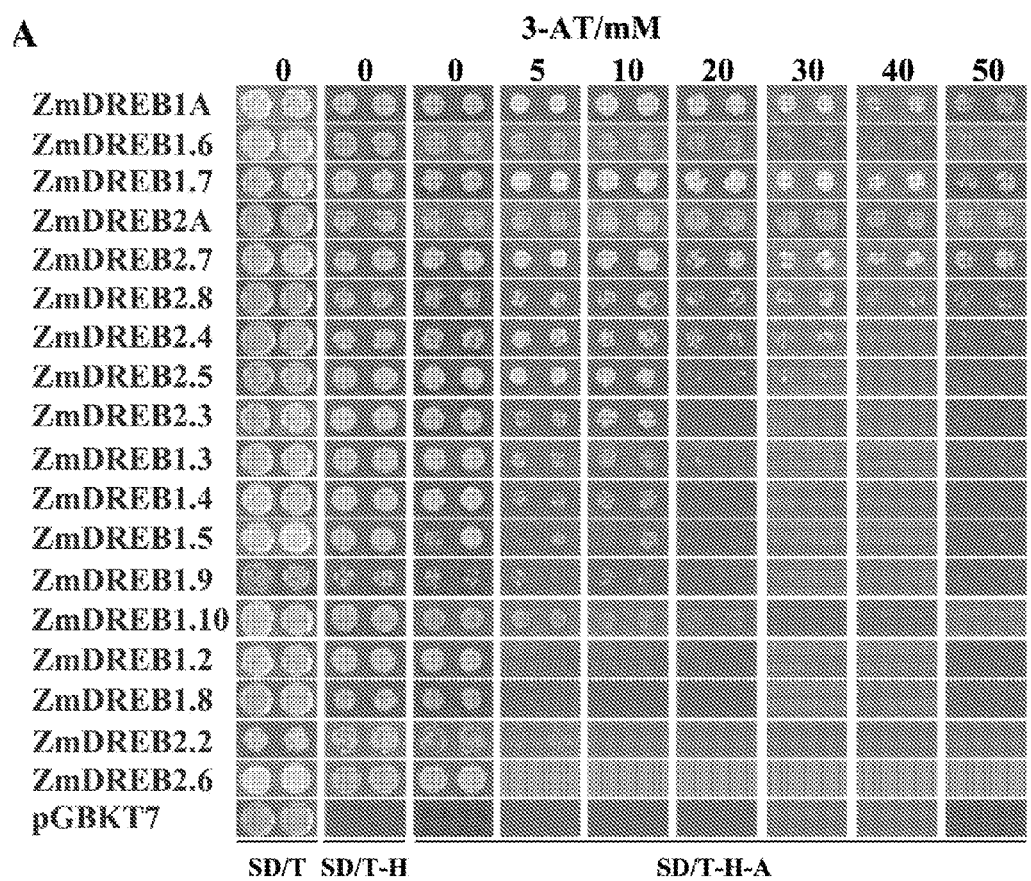
Figure 2B:
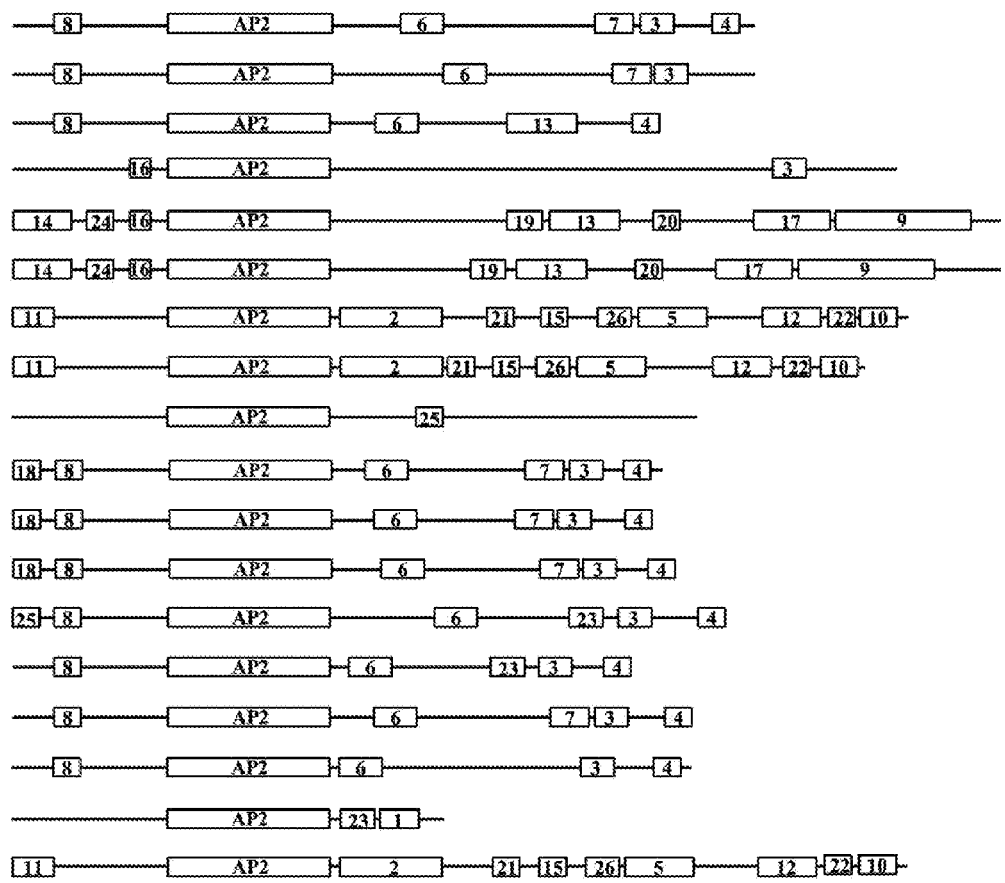

FIG. 2(A)-(B). Transactivation activity assay and motif analysis of 18 ZmDREB proteins.

(A) Cultures of the AH109 yeast, transformed with a plasmid containing different ZmDREB genes, were diluted and inoculated on to a synthetic dropout (SD) media without tryptophan (SD/-T), without tryptophan and histidine (SD/-T-H), or without tryptophan, histidine, and adenine (SD/-T-H-A). The culture plates were amended with different concentrations of 3-aminotriazole (3-AT). Genes were classified into one of three groups (I, II, or III) representing high, medium, or low transactivation activity, respectively. Photos were taken 2 days after inoculation for the plates without 3-AT, and 5 days after inoculation for the plates with various concentrations of 3-AT.

(B) Motif analysis of ZmDREB proteins. Conserved protein motifs were identified using the SALAD database (http://salad.dna.affrc.go.jp/salad/). Different motifs were numbered from 1 to 26 and genes labeled with the same number(s) indicate that the same motif(s) was present in the different ZmDREB proteins. "AP2" denoted the AP2/ERF DNA-binding domains within these proteins. Motifs No. 3, 4, 6, 7, 8 were specific to ZmDREB1 group proteins, except that Motif 3 was also identified in the ZmDREB2.1/2A protein.

Figure 3A:
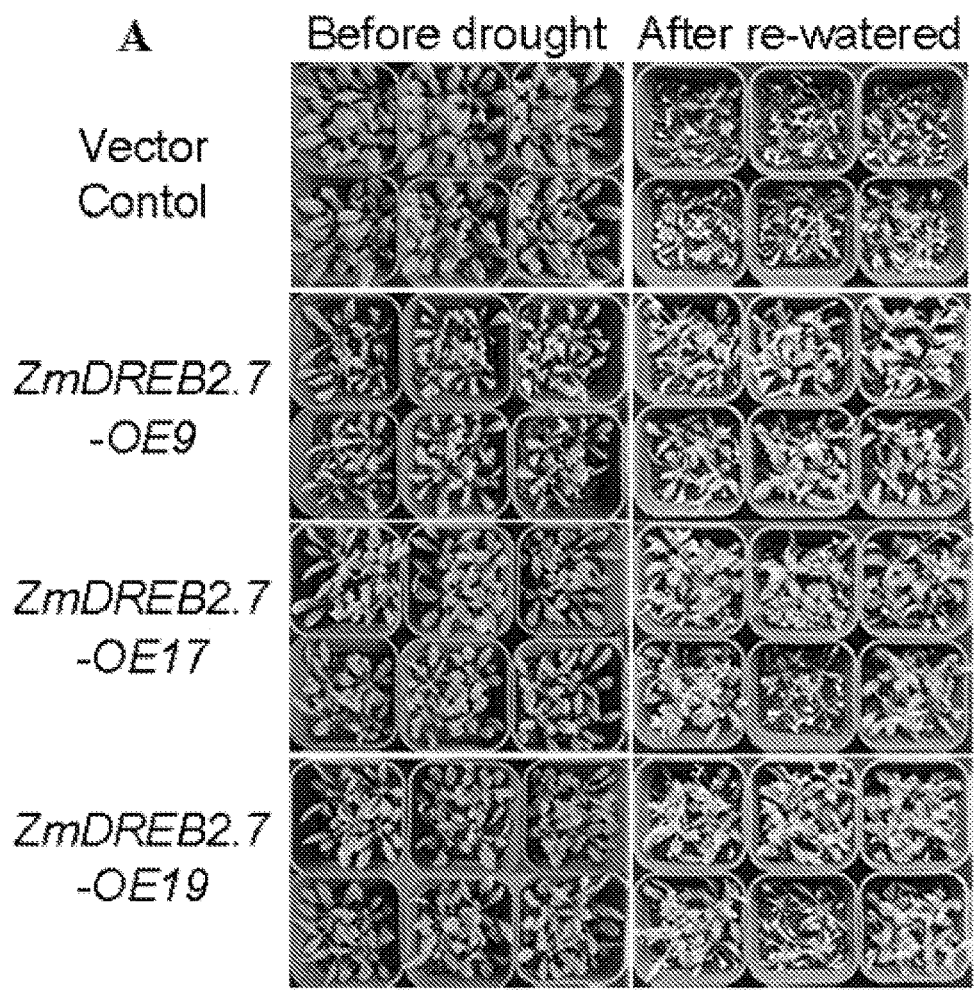

FIG. 3(A)-(C). Drought stress tolerance of 35S:ZmDREB2.7 transgenic *Arabidopsis* plants.

(A) Drought tolerance of transgenic 35S:ZmDREB2.7 *Arabidopsis* plants. Photographs were taken both before and after the drought treatment followed by 6 days rewatering. Vector-transformed plants and ZmDREB2.7-OE9, ZmDREB2.7-OE17 and ZmDREB2.7-OE19 transgenic plants were compared. (B) RT-PCR analysis of transcript levels in the three lines of the 35S:ZmDREB2.7 transgenic plants. (C) Statistical analysis of survival rates after the drought-stress treatment. The average survival rates and standard errors were calculated from three independent experiments. Bars with asterisks indicate lines that had significantly higher survival rates than the vector-transformed plants (t-test, $*p<0.05$).

DETAILED DESCRIPTION OF THE INVENTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous. The practice of the present invention will employ, unless otherwise indicated, conventional techniques of botany, microbiology, tissue culture, molecular biology, chemistry, biochemistry and recombinant DNA technology, bioinformatics which are within the skill of the art. Such techniques are explained fully in the literature.

As used herein, the words "nucleic acid", "nucleic acid sequence", "nucleotide", "nucleic acid molecule" or "polynucleotide" are intended to include DNA molecules (e.g., cDNA or genomic DNA), RNA molecules (e.g., mRNA), natural occurring, mutated, synthetic DNA or RNA molecules, and analogs of the DNA or RNA generated using nucleotide analogs. It can be single-stranded or double-stranded. Such nucleic acids or polynucleotides include, but are not limited to, coding sequences of structural genes, anti-sense sequences, and non-coding regulatory sequences that do not encode mRNAs or protein products. These terms also encompass a gene. The term "gene" or "gene sequence" is used broadly to refer to a DNA nucleic acid associated with a biological function. Thus, genes may include introns and exons as in the genomic sequence, or may comprise only a coding sequence as in cDNAs, and/or may include cDNAs in combination with regulatory sequences. Thus, according to the various aspects of the invention, genomic DNA, cDNA or coding DNA may be used. In one embodiment, the nucleic acid is cDNA or coding DNA. The terms "peptide", "polypeptide" and "protein" are used interchangeably herein and refer to amino acids in a polymeric form of any length, linked together by peptide bonds.

For the purposes of the invention, "transgenic", "transgene" or "recombinant" means with regard to, for example, a nucleic acid sequence, an expression cassette, gene construct or a vector comprising the nucleic acid sequence or an organism transformed with the nucleic acid sequences, expression cassettes or vectors according to the invention, all those constructions brought about by recombinant methods in which either (a) the nucleic acid sequences encoding proteins useful in the methods of the invention, or (b) genetic control sequence(s) which is operably linked with the nucleic acid sequence according to the invention, for example a promoter, or (c) a) and b)

are not located in their natural genetic environment or have been modified by recombinant methods, it being possible for the modification to take the form of, for example, a substitution, addition, deletion, inversion or insertion of one or more nucleotide residues. The natural genetic environment is understood as meaning the natural genomic or chromosomal locus in the original plant or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequences with the corresponding nucleic acid sequence encoding a polypeptide useful in the methods of the present invention, as defined above—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815 both incorporated by reference.

The methods of the invention involve introducing a polypeptide or polynucleotide into a plant. "Introducing" is intended to mean presenting to the plant the polynucleotide or polypeptide in such a manner that the sequence gains access to the interior of a cell of the plant. The methods of the invention do not depend on a particular method for introducing a sequence into a plant, only that the polynucleotide or polypeptides gains access to the interior of at least one cell of the plant. Methods for introducing polynucleotide or polypeptides into plants are known in the art including, but not limited to, breeding methods, stable transformation methods, transient transformation methods, and virus-mediated methods. Methods are known in the art for the targeted insertion of a polynucleotide at a specific location in the plant genome.

A transgenic plant for the purposes of the invention is thus understood as meaning, as above, that the nucleic acids used in the method of the invention are not at their natural locus in the genome of said plant, it being possible for the nucleic acids to be expressed homologously or heterologously. However, as mentioned, transgenic also means that, while the nucleic acids according to the different embodiments of the invention are at their natural position in the genome of a plant, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, preferably, heterologous expression of the nucleic acids takes place. According to the invention, the transgene is stably integrated into the plant and the plant is preferably homozygous for the transgene. Thus, any off spring or harvestable material derived from said plant is also preferably homozygous for the transgene.

The aspects of the invention involve recombination DNA technology and in a preferred embodiment exclude embodiments that are solely based on generating plants by traditional breeding methods.

The inventors have characterized a maize DREB transcription factor (TF) gene, ZmDREB2.7, and have demonstrated that expression of ZmDREB2.7 in transgenic plants confers enhanced drought resistance compared to a control plant.

A control plant as used herein is a plant which has not been modified according to the methods of the invention. Accordingly, the control plant has not been genetically modified to express a nucleic acid as described herein. In one embodiment, the control plant is a wild type plant. In another embodiment, the control plant is a plant that does not carry a transgene according to the methods described herein, but expresses a different transgene. The control plant is typically of the same plant species, preferably the same ecotype as the plant to be assessed.

Thus, in a first aspect, the invention relates to a transgenic plant expressing a nucleic acid construct comprising a ZmDREB2.7 nucleic acid sequence. Thus, the transgenic plant includes within its genome a nucleic acid construct comprising a ZmDREB2.7 nucleic acid sequence. Preferably, said plant is homozygous for the presence of the transgene.

In one embodiment, the ZmDREB2.7 nucleic acid sequence comprises or consists of SEQ ID NO. 1 or 2 or a functional variant thereof. SEQ ID NO. 1 represents both the genomic DNA and the cDNA due to the absence of introns. Residues 99-1178 of that sequence are the coding region (SEQ ID NO. 2). SEQ ID NO. 1 is the nucleotide sequence of ZmDREB2.7 of the inbred maize line B73. The chromosomal region where ZmDREB2.7 is located is chromosome 1, bin 1.07. The accession number is GRMZM2G028386.

The polypeptide encoded by SEQ ID NO: 1 or 2 or a functional variant thereof comprises or consists of SEQ ID NO. 3 or a functional variant thereof. Thus, the transgenic plant of the invention expresses a ZmDREB2.7 nucleic acid sequence and produces a protein that comprises or consists of SEQ ID NO. 4 or a functional variant thereof.

According to the various aspects of the invention, the term "functional variant of a nucleic acid sequence" as used herein, for example with reference to SEQ ID NO: 1, 2 or 3 or homologs thereof, refers to a variant gene sequence or part of the gene sequence which retains the biological function of the full non-variant ZmDREB2.7 gene or ZmDREB2.7 protein sequence, for example confers drought resistance when expressed in a transgenic plant. A functional variant also comprises a variant of the gene of interest encoding a polypeptide which has sequence alterations that do not affect function of the resulting protein, for example in non-conserved residues. Also encompassed is a variant that is substantially identical, i.e. has only some sequence variations, for example in non-conserved residues, to the wild type sequences as shown herein and is biologically active.

Thus, it is understood, as those skilled in the art will appreciate, that the aspects of the invention, including the methods and uses, encompass not only a ZmDREB2.7 nucleic acid or ZmDREB2.7 protein sequence as described herein, for example a nucleic acid sequence comprising or consisting or SEQ ID NO: 1 or 2, a polypeptide comprising or consisting or SEQ ID NO: 3, but also functional variants of a ZmDREB2.7 gene or ZmDREB2.7 protein that do not affect the biological activity and function of the resulting protein. Alterations in a nucleic acid sequence which result in the production of a different amino acid at a given site that do however not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Each of the proposed modifications is well within the routine skill in the art, as is determination of retention of biological activity of the encoded products.

Generally, variants of ZmDREB2.7/ZmDREB2.7 have at least 75% 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% overall sequence identity to the amino acid represented by SEQ ID NO: 1, 2 or 3.

A biologically active variant of a ZmDREB2.7 protein may differ from that protein by as few as 1-15 amino acid residues, as few as 1-10, such as 6-10, as few as 5, as few as 4, 3, 2, or even 1 amino acid residue. In certain embodiments, ZmDREB2.7 proteins may be altered in various ways including amino acid substitutions, deletions, truncations, and insertions. Methods for such manipulations are generally known in the art. For example, amino acid sequence variants and fragments of the ZmDREB2.7 protein can be prepared by mutations in the DNA. Methods for mutagenesis and polynucleotide alterations are well known in the art. See, for example, Kunkel (1985) Proc. Natl. Acad. Sci. USA 82:488-492; Kunkel et al. (1987) Methods in Enzymol. 154:367-382; U.S. Pat. No. 4,873,192; Walker and Gaastra, eds. (1983) Techniques in Molecular Biology (MacMillan Publishing Company, New York) and the references cited therein. The deletions, insertions, and substitutions of the protein sequences encompassed herein are not expected to produce radical changes in the characteristics of the protein. When it is difficult, however, to predict the exact effect of a substitution, deletion, or insertion in advance of making such modifications, one skilled in the art will appreciate that the effect will be evaluated by routine screening assays.

For example, sequence identity/similarity values provided herein can refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof.

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percentage sequence identity may be adjusted upwards to correct for the conservative nature of the substitution. Sequences that differ by such conservative substitutions are said to have "sequence similarity" or "similarity".

Also, the various aspects of the invention the aspects of the invention, including the methods and uses, encompass not only a ZmDREB2.7 nucleic acid sequence as shown herein, but also a fragment thereof. By "fragment" is intended a portion of the nucleotide sequence or a portion of the amino acid sequence and hence of the protein encoded thereby. Fragments of a nucleotide sequence may encode protein fragments that retain the biological activity of the native protein and hence confer drought resistance.

The ZmDREB2.7 amino acid sequence encoded by SEQ ID NO. 1 or 2 or a functional variant thereof (SEQ ID NO. 3) is characterised by the presence of conserved motifs as shown in FIG. 2B. In a functional ZmDREB2.7 variant protein, changes to the amino acid sequence are preferably located outside these domains.

These conserved motifs present in the ZmDREB2.7 protein comprise the following sequences:

Motif 14: QQQQQFVHHLQQVHQQGTQHEQ (SEQ ID NO. 16) or a sequence with at least 95%, 96%, 97%, 98% or 99% homology thereto;

Motif 24: GRKCCPLR (SEQ ID NO. 17) or a sequence with at least 98% or 99% homology thereto;

Motif 16: RSRKGCMK (SEQ ID NO. 18) or a sequence with at least 98% or 99% homology thereto;

AP2 domain: PFRGVRQRTWGKWVAEIREPNRGARLWLGTFGSALEAARAYDAAARTLYGDCARLNLQ (SEQ ID NO. 19) or a sequence with at least 95%, 96%, 97%, 98% or 99% homology thereto;

Motif 19: HNCHHQYLQQQ (SEQ ID NO. 20) or a sequence with at least 98% or 99% homology thereto;

Motif 13: MAAPMMMMHSSCCSADGSSSNSDSISNS (SEQ ID NO. 21) or a sequence with at least 95%, 96%, 97%, 98% or 99% homology thereto;

Motif 20: YSHHQTMFQT (SEQ ID NO. 22) or a sequence with at least 98% or 99% homology thereto;

Motif 17: DDDTTTAMAMHRHQQMMRELAEAPLHQE (SEQ ID NO. 23) or a sequence with at least 98% or 99% homology thereto;

Motif 9: DDFEDFVTRLPKAEDFGLQGFQEVAPEVFDDAAGIWDHAAAWEPPTMMID (SEQ ID NO. 24) or a sequence with at least 95%, 96%, 97%, 98% or 99% homology thereto;

In one aspect, the various aspects of the invention also relate to a ZmDREB2.7 homolog/ortholog in another species wherein the nucleic acid sequence of said homolog comprises sequences with at least 95%, 96%, 97%, 98% or 99% or sequences with 100% homology to each of motifs 14, 24, 16, 19, 13, 20, 17, 9 and to the AP2 domain. Accordingly, the method and uses described herein also extend to such homolog.

In one embodiment according to the various aspects of the invention, the nucleic acid construct comprises a regulatory sequence or element. According to the various aspects of the invention, the term "regulatory element" is used interchangeably herein with "control sequence" and "promoter" and all terms are to be taken in a broad context to refer to regulatory nucleic acid sequences capable of effecting expression of the sequences to which they are ligated. The term "regulatory element" also includes terminator sequences which may be included 3' of the ZmDREB2.7 nucleic acid sequence. The term "promoter" typically refers to a nucleic acid control sequence located upstream from the transcriptional start of a gene and which is involved in recognising and binding of RNA polymerase and other proteins, thereby directing transcription of an operably linked nucleic acid. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences.

The term "regulatory element" also encompasses a synthetic fusion molecule or derivative that confers, activates or enhances expression of a nucleic acid molecule in a cell, tissue or organ.

A "plant promoter" comprises regulatory elements, which mediate the expression of a coding sequence segment in plant cells. Accordingly, a plant promoter need not be of plant origin, but may originate from viruses or microorganisms, for example from viruses which attack plant cells. The "plant promoter" can also originate from a plant cell, e.g. from the plant which is transformed with the nucleic acid sequence to be expressed in the inventive process and described herein. This also applies to other "plant" regulatory signals, such as "plant" terminators. The promoters upstream of the nucleotide sequences useful in the methods of the present invention can be modified by one or more nucleotide substitution(s), insertion(s) and/or deletion(s) without interfering with the functionality or activity of either the promoters, the open reading frame (ORF) or the 3'-regulatory region such as terminators or other 3' regulatory regions which are located away from the ORF. It is furthermore possible that the activity of the promoters is increased by modification of their sequence, or that they are replaced completely by more active promoters, even promoters from heterologous organisms. For expression in plants, the nucleic acid molecule must, as described above, be linked operably to or comprise a suitable promoter which expresses the gene at the right point in time and with the required spatial expression pattern. For the identification of functionally equivalent promoters, the promoter strength and/or expression pattern of a candidate promoter may be analysed for example by operably linking the promoter to a reporter gene and assaying the expression level and pattern of the reporter gene in various tissues of the plant. Suitable well-known reporter genes are known to the skilled person and include for example beta-glucuronidase or beta-galactosidase.

The ZmDREB2.7 nucleic acid is operably linked to a regulatory sequence or element. The term "operably linked" as used herein refers to a functional linkage between the promoter sequence and the gene of interest, such that the promoter sequence is able to initiate transcription of the gene of interest.

In one preferred embodiment, the nucleic acid sequence may be expressed using a promoter that drives overexpression. Overexpression according to the invention means that the transgene is expressed at a level that is higher than expression of endogenous counterparts driven by their endogenous promoters. For example, overexpression may be carried out using a strong promoter, such as a constitutive promoter. A "constitutive promoter" refers to a promoter that is transcriptionally active during most, but not necessarily all, phases of growth and development and under most environmental conditions, in at least one cell, tissue or organ. Examples of constitutive promoters include the cauliflower mosaic virus promoter (CaMV35S or 19S), rice actin promoter, maize ubiquitin promoter, rubisco small subunit, maize or alfalfa H3 histone, OCS, SAD1 or 2, GOS2 or any promoter that gives enhanced expression. Alternatively, enhanced or increased expression can be achieved by using transcription or translation enhancers or activators and may incorporate enhancers into the gene to further increase expression. Furthermore, an inducible expression system may be used, where expression is driven by a promoter induced by environmental stress conditions, in particular drought. The promoter may also be tissue-specific. The types of promoters listed above are described in the art. Other suitable promoters and inducible systems are also known to the skilled person.

In a one embodiment, the promoter is a constitutive or strong promoter. In one embodiment, the promoter is CaMV35S.

In one embodiment, the promoter is a ZmDREB2.7 promoter isolated from a drought tolerant maize inbred line (SEQ ID No. 4). Such promoter that comprises one or more, preferably all polymorphisms at the following positions: SNP-503, SNP-260, InDel-185, InDel-154 and SNP-150, located upstream of the ATG site with respect to SEQ ID NO. 2 (the A in the ATG site is designated as +1; this is the first residue in SEQ ID NO. 2) compared to a drought sensitive line. In particular, this promoter can be used to confer expressing at the onset of drought stress.

Additional nucleic acid sequences which facilitate cloning of the target nucleic acid sequences into an expression vector may also be included in the nucleic acid construct according to the various aspects of the invention. This encompasses the alteration of certain codons to introduce specific restriction sites that facilitate cloning. A terminator sequence may also be included in the construct.

In one embodiment, the plant is maize and the nucleic acid construct comprising ZmDREB2.7 may be expressed in a maize plant by recombinant methods. In another embodiment, an exogenous ZmDREB2.7 nucleic acid is expressed in a second plant of another species by recombinant methods. Thus, all aspects of the invention, including the transgenic plants and methods of the invention, also extend to plants other than maize which express a nucleic acid construct comprising a ZmDREB2 nucleic acid sequence.

In one embodiment, the plant is a monocot or dicot plant. In one embodiment, the plant is a crop plant or biofuel plant.

In one embodiment of the various aspects of the invention, the plant is a dicot plant. A dicot plant may be selected from the families including, but not limited to Asteraceae, Brassicaceae (eg *Brassica napus*), Chenopodiaceae, Cucurbitaceae, Leguminosae (Caesalpiniaceae, Aesalpiniaceae Mimosaceae, Papilionaceae or Fabaceae), Malvaceae, Rosaceae or Solanaceae. For example, the plant may be selected from lettuce, sunflower, *Arabidopsis*, broccoli, spinach, water melon, squash, cabbage, tomato, potato, yam, capsicum, tobacco, cotton, okra, apple, rose, strawberry, alfalfa, bean, soybean, field (fava) bean, pea, lentil, peanut, chickpea, apricots, pears, peach, grape vine or citrus species. In one embodiment, the plant is oilseed rape.

Also included are biofuel and bioenergy crops such as rape/canola, corn, sugar cane, palm trees, jatropha, soybeans, sorghum, sunflowers, cottonseed, *Panicum virgatum* (switchgrass), linseed, wheat, lupin and willow, poplar, poplar hybrids, *Miscanthus* or gymnosperms, such as loblolly pine. Also included are crops for silage (maize), grazing or fodder (grasses, clover, sanfoin, alfalfa), fibres (e.g. cotton, flax), building materials (e.g. pine, oak), pulping (e.g. poplar), feeder stocks for the chemical industry (e.g. high erucic acid oil seed rape, linseed) and for amenity purposes (e.g. turf grasses for golf courses), ornamentals for public and private gardens (e.g. snapdragon, petunia, roses, geranium, *Nicotiana* sp.) and plants and cut flowers for the home (African violets, Begonias, chrysanthemums, geraniums, Coleus spider plants, Dracaena, rubber plant).

In one embodiment of the various aspects of the invention, the plant is a dicot plant. A monocot plant may, for example, be selected from the families Arecaceae, Amaryllidaceae or Poaceae. For example, the plant may be a cereal crop, such as wheat, rice, barley, maize, oat, sorghum, rye, millet, buckwheat, turf grass, Italian rye grass, sugarcane or *Festuca* species, or a crop such as onion, leek, yam or banana.

In preferred embodiments of the various aspects of the invention the plant is a crop plant. By crop plant is meant any plant which is grown on a commercial scale for human or animal consumption or use.

In preferred embodiments of the various aspects of the invention the plant grain plant, an oil-seed plant, and a leguminous plant.

Most preferred plants according to the various aspects of the invention are maize, rice, wheat, oilseed rape, sorghum, soybean, potato, tomato, tobacco, grape, barley, pea, bean, field bean, lettuce, cotton, sugar cane, sugar beet, broccoli or other vegetable brassicas or poplar.

The term "plant" as used herein encompasses whole plants, ancestors and progeny of the plants and plant parts, including seeds, fruit, shoots, stems, leaves, roots (including tubers), flowers, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again wherein each of the aforementioned comprises the gene/nucleic acid of interest.

The term "maize" as used herein refers to a plant of the *Zea mays* L. ssp. *mays* and is also known as "corn". The term "maize plant" includes: whole maize plants, maize germplasm, maize plant cells, maize plant protoplast, maize plant cell or maize tissue cultures from which maize plants can be regenerated, maize plant calli, and maize plant cells that are intact in maize plants or parts of maize plants, such as maize seeds, maize cobs, maize flowers, maize cotyledons, maize leaves, maize stems, maize buds, maize roots, maize root tips, and the like. The maize can be an inbred line, or a maize hybrid such as a maize single cross hybrid.

The various aspects of the invention described herein clearly extend to any plant cell or any plant produced, obtained or obtainable by any of the methods described herein, and to all plant parts and propagules thereof unless otherwise specified. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced by the parent in the methods according to the invention.

The invention also extends to harvestable parts of a plant of the invention as described above such as, but not limited to seeds, leaves, fruits, flowers, stems, roots, rhizomes, tubers and bulbs. The invention furthermore relates to products derived, preferably directly derived, from a harvestable part of such a plant, such as dry pellets or powders, oil, fat and fatty acids, starch or proteins. The invention also relates to products, including food products and food supplements comprising the plant of the invention or parts thereof.

The plant according to the invention shows increased resistance to drought or water deficiency compared to a control plant (see FIG. 3(A)-(C)).

In one embodiment, said stress is moderate or severe stress. A plant according to the invention also shows reduced growth/yield penalties under moderate stress compared to a control plant.

In one embodiment, the methods of the invention thus relate to increasing resistance to moderate (non-lethal) stress or severe stress. In the former embodiment, transgenic plants according to the invention show increased resistance to stress and therefore, the plant yield is not or less affected by the stress compared to wild type yields which are reduced upon exposure to stress. In other words, an improve in yield under moderate stress conditions can be observed.

For example, drought tolerance is assessed predominantly under quite severe conditions in which plant survival is scored after a prolonged period of soil drying. However, in temperate climates, limited water availability rarely causes plant death, but restricts biomass and seed yield. Moderate water stress, that is suboptimal availability of water for growth can occur during intermittent intervals of days or weeks between irrigation events and may limit leaf growth, light interception, photosynthesis and hence yield potential. Leaf growth inhibition by water stress is particularly undesirable during early establishment. There is a need for methods for making plants with increased yield under moderate stress conditions. In other words, whilst plant research in making stress tolerant plants is often directed at identifying plants that show increased stress tolerance under severe conditions that will lead to death of a wild type plant, these plants do not perform well under moderate stress conditions and often show growth reduction which leads to unnecessary yield loss. Thus, in one embodiment of the methods of the invention, yield is improved under moderate stress conditions. The transgenic plants according to the various aspects of the invention show enhanced tolerance to these types of stresses compared to a control plant and are able to mitigate any loss in yield/growth. The tolerance can therefore be measured as an increase in yield as shown in the examples. The terms moderate or mild stress/stress conditions are used interchangeably and refer to non-severe stress. In other words, moderate stress, unlike severe stress, does not lead to plant death. Under moderate, that is non-lethal, stress conditions, wild type plants are able to survive, but show a decrease in growth and seed production and prolonged moderate stress can also result in developmental arrest. The decrease can be at least 5%-50% or more. Tolerance to severe stress is measured as a percentage of survival, whereas moderate stress does not affect survival, but growth rates. The precise conditions that define moderate stress vary from plant to plant and also between climate zones, but ultimately, these moderate conditions do not cause the plant to die.

Generally speaking, moderate drought stress is defined by a water potential of between −1 and −2 Mpa.

In one embodiment, the maize relative leaf water content (RLWC) at 95-100% is well-watered or favourable growth condition; RLWC at around 70-65% is moderate drought stress; RLWC at around 58-55% is severe drought stress.

Drought tolerance can be measured using methods known in the art, for example assessing survival of the transgenic plant compared to a control plant, through leaf water potentials or by determining turgor pressure, rosette radius, water loss in leaves, growth or yield. Drought resistance can also be measured by assessing stomatal conductance (Gst) and transpiration in whole plants under basal conditions.

According to the invention, a transgenic plant has enhanced drought tolerance if the survival rates are at least 2, 3, 4, 5, 6, 7, 8, 9 or 10-fold higher than those of the control plant after exposure to drought and/or after exposure to drought and re-watering. Also according to the invention, a transgenic plant has enhanced drought tolerance if the rosette radius is at least 10, 20, 30, 40, 50% larger than that of the control plant after exposure to drought and/or after exposure to drought and re-watering. The plant may be deprived of water for 10-30, for example 20 days and then re-watered. Also according to the invention, a transgenic plant has enhanced drought tolerance if stomatal conductance (Gst) and transpiration are lower than in the control plant, for example at least 10, 20, 30, 40, 50% lower.

The terms "increase", "improve" or "enhance" are interchangeable. Yield for example is increased by at least a 3%, 4%, 5%, 6%, 7%, 8%, 9% or 10%, preferably at least 15% or 20%, more preferably 25%, 30%, 35%, 40% or 50% or more in comparison to a control plant. The term "yield" in general means a measurable produce of economic value, typically related to a specified crop, to an area, and to a period of time. Individual plant parts directly contribute to yield based on their number, size and/or weight, or the actual yield is the yield per square meter for a crop and year, which is determined by dividing total production (includes both harvested and appraised production) by planted square meters. The term "yield" of a plant may relate to vegetative biomass (root and/or shoot biomass), to reproductive organs, and/or to propagules (such as seeds) of that plant. Thus, according to the invention, yield comprises one or more of and can be measured by assessing one or more of: increased seed yield per plant, increased seed filling rate, increased number of filled seeds, increased harvest index, increased number of seed capsules/pods, increased seed size, increased growth or increased branching, for example inflorescences with more branches. Preferably, yield comprises an increased number of seed capsules/pods and/or increased branching. Yield is increased relative to control plants.

In another aspect, the invention relates to an isolated nucleic acid comprising or consisting of SEQ ID NO. 1 or 2 or a functional variant thereof. In another aspect, the invention relates to an isolated amino acid sequence comprising or consisting of SEQ ID NO. 3 or a functional variant thereof.

In another aspect, the invention relates to a vector comprising a nucleic acid construct comprising SEQ ID NO. 1 or 2 or a functional variant thereof. In one embodiment, said vector is an expression vector. Expression vectors for expressing nucleic acid sequences in a plant are well known. An example is pGXX. For example, a ZmDREB2.7 nucleic acid sequence as described herein can be inserted between the SmaI and SalI restriction sites of the pGXX vector. Plant expression vectors also include dual *agrobacterium* vectors and plant micro bombardment vectors such as pROKII, pBin438, pCAMBIA1302, pCAMBIA2301, pCAMBIA1301, pCAMBIA1300, pBI121, pCAMBIA1391-Xa or pCAMBIA1391-Xb.

The vector may further comprise a regulatory sequence which directs expression of the nucleic acid. Such sequences are described elsewhere herein. In one example, the regulatory sequence is a promoter that directs overexpression of the nucleic acid sequence. Marker genes (e.g Gus) and resistance genes can also be included.

In another aspect, the invention relates to a host cell comprising a vector as described herein. The host cell can be selected from a plant cell or a bacterial cell, for example *Agrobacterium*. The invention also relates to a culture medium or kit comprising a culture medium and an isolated host cell as described above.

In another aspect, the invention relates to the use of a nucleic acid construct comprising or consisting of SEQ ID NO. 1 or 2 or a functional variant thereof or a vector described herein in conferring drought resistance to a plant.

In another aspect, the invention relates to the use of a nucleic acid construct comprising or consisting SEQ ID NO. 1 or 2 or a functional variant thereof or a vector described herein in increasing yield/growth of a plant under drought stress conditions.

In another aspect, the invention relates to a method for conferring to or increasing drought resistance of a plant said method comprising introducing and expressing in said plant a nucleic acid construct comprising or consisting of SEQ ID NO. 1 or 2 or a functional variant thereof. In another aspect, the invention relates to a method for increasing yield of a plant, for example under moderate drought stress, said method comprising introducing and expressing in said plant a nucleic acid construct comprising or consisting of SEQ ID NO. 1 or 2 or a functional variant thereof.

The term plant is defined elsewhere herein.

In one embodiment, said construct further comprises a regulatory sequence. Such sequences are described elsewhere herein. In one example, the regulatory sequence is a promoter that directs overexpression of the nucleic acid sequence.

The nucleic acid or vector described above is used to generate transgenic plants using transformation methods known in the art. Thus, according to the various aspects of the invention, a nucleic acid comprising a ZmDREB2.7 nucleic acid or a functional variant thereof is introduced into a plant and expressed as a transgene. The nucleic acid sequence is introduced into said plant through a process called transformation. The term "introduction" or "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation. Transformation of plants is now a routine technique in many species. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts, electroporation of protoplasts, microinjection into plant material, DNA or RNA-coated particle bombardment, infection with (non-integrative) viruses and the like. Transgenic plants, including transgenic crop plants, are preferably produced via *Agrobacterium tumefaciens* mediated transformation.

To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility is growing the seeds, if appropriate after sterilization, on agar plates using a suitable selection agent so that only the transformed seeds can grow into plants. Alternatively, the transformed plants are screened for the presence of a selectable marker such as the ones described above. Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The invention relates to a method for producing a transgenic plant with improved drought resistance compared to a control plant comprising
  a) introducing into said plant and expressing a nucleic acid construct comprising a ZmDREB2.7 nucleic acid sequence, for example a nucleic acid sequence comprising SEQ ID NO: 1 or 2 a functional variant of SEQ ID NO: 1 or 2 and
  b) obtaining a progeny plant derived from the plant or plant cell of step a).

Thus, the invention relates to a method for producing a transgenic plant with improved yield under water deficiency or drought stress comprising
  a) introducing into said plant and expressing a nucleic acid construct comprising a ZmDREB2.7 nucleic acid sequence, for example a nucleic acid sequence comprising SEQ ID NO: 1 or 2 a functional variant of SEQ ID NO: 1 or 2 and
  b) obtaining a progeny plant derived from the plant or plant cell of step a).

In one embodiment, the drought stress is moderate.

The methods above may comprise the further steps of:
  detecting the presence of the transgene by methods known in the art;
  exposing the plant to stress conditions, such as drought; assessing yield/growth;
  selecting a plant or part thereof with increased stress resistance/improved yield/growth;
  optionally harvesting parts of the plant.

The invention also relates to plants obtained or obtainable with said method. The term plant is defined elsewhere herein.

The invention also relates to a plant with increased expression of an endogenous nucleic acid as defined in SEQ ID NO. 1 or 2 or a functional variant thereof wherein said endogenous promoter carries a mutation introduced by mutagenesis or genome editing which results in increased expression of the nucleic acid as defined in SEQ ID NO. 1 or 2 or a functional variant thereof.

The invention also relates to a method for increasing expression of a nucleic acid as defined in SEQ ID NO. 1 or 2 or a functional variant thereof in a plant, producing plants, a method for mitigating the impacts of stress conditions on plant growth and yield and a method for producing plants with improved yield/growth under stress conditions comprising the steps of mutagenising a plant population, identifying and selecting plants with an improved yield/growth under stress conditions and identifying a variant ZmDREB2.7 promoter sequence which directs expression of a nucleic acid as defined in SEQ ID NO. 1 or 2 or a functional variant thereof.

The above can be achieved using targeted genome edition, for example by using CRISPR or TALEN.

While the foregoing disclosure provides a general description of the subject matter encompassed within the scope of the present invention, including methods, as well as the best mode thereof, of making and using this invention, the following examples are provided to further enable those skilled in the art to practice this invention and to provide a complete written description thereof. However, those skilled in the art will appreciate that the specifics of these examples should not be read as limiting on the invention, the scope of which should be apprehended from the claims and equivalents thereof appended to this disclosure. Various further aspects and embodiments of the present invention will be apparent to those skilled in the art in view of the present disclosure.

All documents mentioned in this specification, including reference to sequence database identifiers, are incorporated herein by reference in their entirety. Unless otherwise specified, when reference to sequence database identifiers is made, the version number is 1.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described. The invention is further described in the following non-limiting examples.

BRIEF DESCRIPTION OF THE PREFERRED EMBODIMENTS

Examples

Example 1: Obtaining the ZmDREB2.7 Protein and its Genetic Coding

Taking seeds of the B73 maize inbred line, these were allowed to germinate at 28° C. for three days, then the seeds that had germinated were transferred to nutrient soil or nutrient liquid and grown for three weeks. The whole plants were quick-frozen using liquid nitrogen, then ground up, and the total RNA extracted. Reverse transcription was carried out, yielding cDNA, then the cDNA was used as the template, and 5'-ATGGATCGGGTGCCGCCG-3' (SEQ ID NO. 10) and 5'-TCAAAGAGGGACGACGAGC-3' (SEQ ID NO. 11) used as the primers and PCR amplification performed. The amplified result was then subjected to agarose gel electrophoresis, and the separated purified 1.1 kb DNA segment subjected to sequencing; the resulting DNA segment sequence is that indicated between the 99th-1178 position in sequence 2 in the sequence table.

SEQ ID NO. 1 in the sequence table is the full length cDNA of the B73 maize inbred line of the ZmDREB2.7 protein indicated by sequence 4. Residues 1st-98th of SEQ ID NO. 1 are non-coding regions, residues 99th-1178th are the coding sequence, and residues 1179th-1584th are the 3' non-coding region.

In order to facilitate the purification of the ZmDREB2.7 protein, a marker as shown in table 1 may be attached to the amino terminal or carboxyl terminal of the protein.

TABLE 1

| Marker | Residue | Sequence | |
|---|---|---|---|
| Poly-Arg | 5-6 (generally 5) | RRRRR | SEQ ID NO: 5 |
| Poly-His | 2-10 (generally 6) | HHHHHH | SEQ ID NO: 6 |
| FLAG | 8 | DYKDDDDK | SEQ ID NO: 7 |
| Strep-tag II | 8 | WSHPQFEK | SEQ ID NO: 8 |
| c-myc | 10 | EQKLISEEDL | SEQ ID NO: 9 |

The protein in (b) above may be artificially synthesised. Alternatively, its genetic code may be synthesised first, then it may be obtained by biological expression.

Example 2: Phylogenetic Tree Construction

Figure 1:
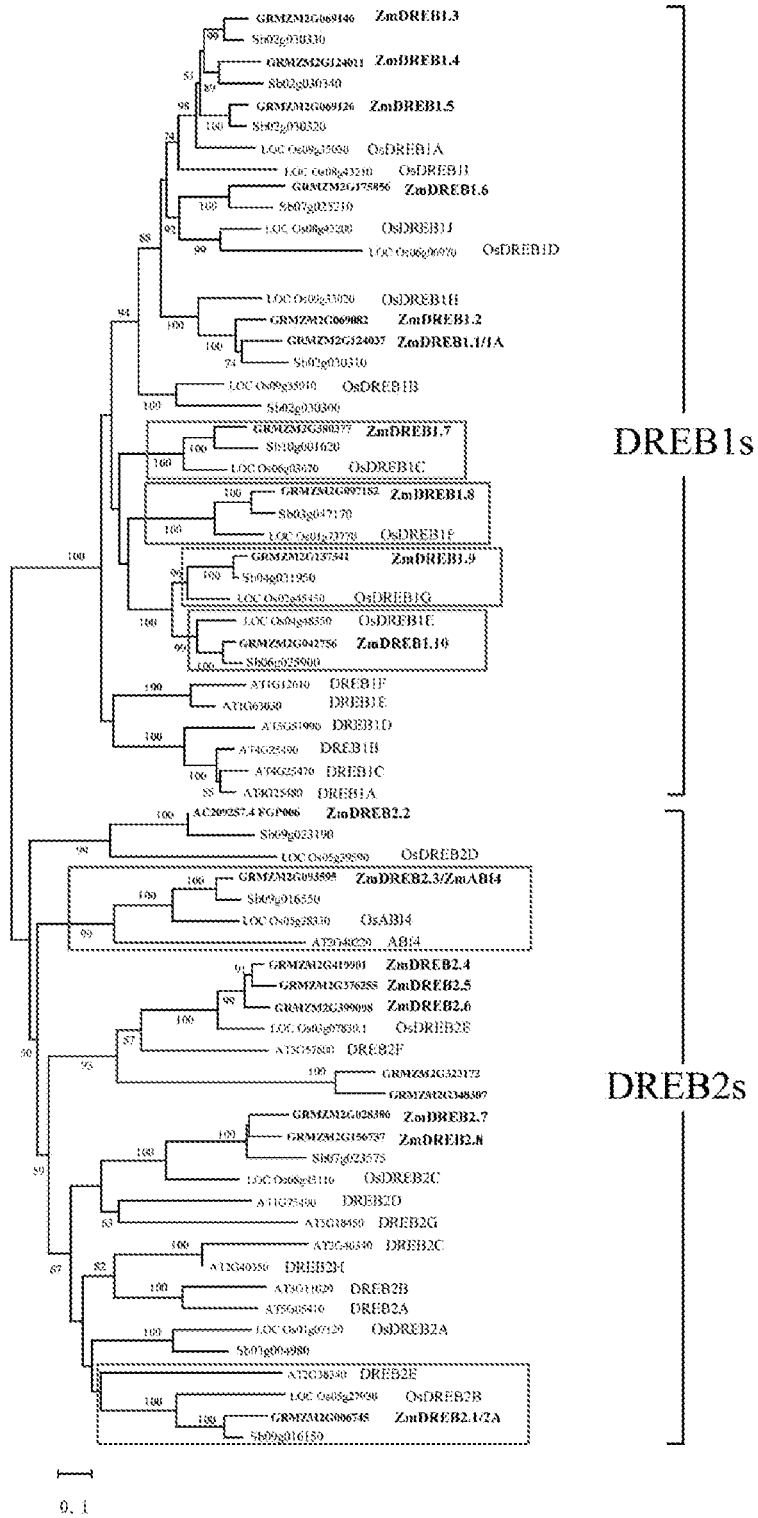
FIG. 1. Phylogenetic tree of canonical DREB1 and DREB2 genes in maize, rice, sorghum and *Arabidopsis*.

Full-length amino acid sequences of 66 DREB1s and DREB2s identified in maize, rice, *Arabidopsis* and sorghum were aligned using the Clustal X 1.83 program with default pairwise and multiple alignment parameters. The phylogenetic tree was constructed based on this alignment result using the neighbor joining (NJ) method in MEGA version 5 (http://www.megasoftware.net/) with the following parameters: Poisson correction, pairwise deletion, uniform rates and bootstrap (1000 replicates). The ZmDREB proteins were named sequentially according to their placement in the phylogenetic tree (see FIG. 1).

Example 3: Transactivation Activity Assay

Eighteen ZmDREB genes were individually cloned into the pBluescript II KS+ vector from the maize B73 inbred line. After sequence analysis, the ZmDREB genes were transferred topGBKT7 for evaluation of transactivation activity in the AH109 yeast strain. The cell concentration of yeast transformants was adjusted to an OD600 of 0.1, the yeast cells were then dropped on SD/-T, SD/-T-H, SD/-T-H-A and SD/-T-H-A plates containing various concentrations of 3-AT to compare their ability to grow. The plates were incubated at 30 uC for 2-5 days before photographing.

Example 4: Overexpression of the ZmDREB2.7 Gene to Increase Drought Resistance of *Arabidopsis thaliana*, Binding Assay and Protein Analysis The DNA segment indicated in the 99th-1178th position of sequence 2 in the sequence table was cloned onto the enzyme digestion loci Sma I and Sal I (downstream from the 35S promoter) of the pGKX vector, then sequencing was carried out confirming that the pGZ recombinant vector had been obtained. The coding region of the ZmDREB2.7 cDNA of the maize B73 inbred line (1080 bp), digested with Sma I and Sal I (Takara), was inserted into the pGreen0029-35S-Ω vector [11]. The constructed plasmid carrying the desired gene was transformed into *Agrobacterium tumefaciens* GV3101+pSoup. *Arabidopsis thaliana* ecotype Col-0 was transformed as described previously [6].

Using kanamycin-based selection, several independent T2 transgenic lines were obtained, and expression of ZmDREB2.7 transgene was confirmed in these lines by RT-PCR.

The sequences the primers used in the RT-PCR are as follows:

F1:
(SEQ ID NO. 12)
5'-TATGATGATGATGCACTCC-3'

R1:
(SEQ ID NO. 13)
5'-GAGTTGGAAATGGAATCG-3'

FC:
(SEQ ID NO. 14)
5'-GGTAACATTGTGCTCAGTGGTGG-3'

RC:
(SEQ ID NO. 15)
5'-GCATCAATTCGATCACTCAGAG-3'

The results as shown in FIG. 3(A)-(C) indicate that the CK strain does not express the target gene ZmDREB2.7; however, the expression of the ZmDREB2.7 target gene in the transgenic ZmDREB2.7 *Arabidopsis* strains TL1-TL3 is very high. Three independent homozygous $T_3$ overexpression lines ZmDREB2.7-OE9, ZmDREB2.7-OE17 and ZmDREB2.7-OE19 were selected based on the level of transgene expression and subjected to further analyses. Control plants were homozygous from the empty vector (CK).

Seven-day-old plants were transferred into pots containing 100 g soil/pot. Thirty two-day-old plants growing under favorable water conditions were exposed to drought stress. Water was withheld from the plants for 14 days. Watering was then resumed to allow plants to recover. Six days later, the number of surviving plants was recorded. At least 30 plants of each line were compared with WT in each test and statistical data were obtained from three independent experiments. After 14 days there was a pronounced difference between the phenotypes, the rosette leaves of the CK strain exhibiting severe withering, the rosette leaves of the TL1-TL3 strains exhibiting severe wilting, then watering was recommenced. Six days after watering was recommenced, the survival rate of each strain was calculated (plants which grew normally and from which seeds could be harvested were defined as surviving plants, those severely damaged by drought and which were unable to grow normally and from which seeds could not be harvested being defined as dead plants; the survival rate being the percentage of surviving plants of a particular strain out of the total number of plants of that strain). The experiment was repeated 3 times, and on each occasion the number of plants for each strain was not less than 30, then the averages obtained and used for statistical analysis purposes. The results are shown in table 2 and FIG. 3(A)-(C).

TABLE 2

Survival rate (%) of transgenic *Arabidopsis* plants after drought treatment

| Strain | Repetition 1 | Repetition 2 | Repetition 3 | Average +/− standard deviation |
|---|---|---|---|---|
| TL1 | 100 | 93.75 | 96.88 | 96.87 +/− 3.13** |
| TL2 | 81.25 | 98.08 | 63.64 | 80.99 +/− 17.22* |
| TL3 | 80.00 | 83.33 | 82.69 | 82 +/− 1.77** |
| CK | 41.07 | 36.11 | 27.78 | 34.99 +/− 6.72 |

Note:
*indicates significant difference <0.05 when compared with CK results,
**indicates significant difference P < 0.01 when compared with CK results.

ZmDREB2.7 binding assays to determine binding to the DRE sequences were also carried out showing that ZmDREB2.7 can bind the DRE Sequence. Although the DNA binding preference of ZmDREB2.1/2A and ZmDREB2.7 is generally similar, at a low protein concentration ZmDREB2.1/2A showed a higher affinity for the DRE sequences than ZmDREB2.7. DREB proteins function as transactivators that regulate the transcription of downstream target genes in response to abiotic stress. The transactivation activity of each ZmDREB protein was also characterized using a yeast activation assay. Results indicated that the ZmDREB proteins can be classified into three groups based upon their levels of transactivation activity. Three ZmDREB1 (1.1/1A, 1.7, 1.6) and four ZmDREB2 (2.1/2A, 2.4, 2.7, 2.8) proteins exhibited the highest level of transactivation activity. Five ZmDREB1 (1.3, 1.4, 1.5, 1.9, 1.10), ZmDREB2.5, and ZmDREB2.3/ZmABI4 proteins exhibit moderate levels of transactivation activity as determined by their ability to grow well on the selective medium amended with 10 mM 3-AT. Lastly, four ZmDREB1 (1.2, 1.8, 2.2, and 2.6) proteins exhibited minimal transactivation activity as the yeast cells transformed by these plasmids could only grow on a medium without 3-AT.

In order to gain insight into the differences in transactivation activity exhibited by the ZmDREB proteins, the sequence similarity between all of the proteins was examined (FIG. 2B). In addition to the conserved AP2/ERF DNA-binding domain, all of the ZmDREB1 s proteins commonly shared a number of conserved motifs, such as motifs 3, 4, 6, 7 and 8. The sequences of ZmDREB2 proteins, however, were more diversified in relative comparison to ZmDREB1 proteins. ZmDREB2.1/2A contained motif 3 which was present only in DREB1 proteins but absent in the other ZmDREB2 proteins. ZmDREB2.7 and 2.8, which displayed high transactivation activity, shared a similar motif structure. Motif 13, found in these two proteins, was also present in ZmDREB1.7 but not in any other proteins. Although the motif composition of ZmDREB2.4, 2.5 and 2.6 were highly conserved, the protein transactivation activity of ZmDREB2.6 was much lower than ZmDREB2.4 and 2.5. Therefore, other unconserved regions or some key amino acid residues of these proteins may be responsible for the observed differences in protein activity. ZmDREB2.3/ZmABI4 and ZmDREB2.2 share little similarity to the other ZmDREB proteins. These results demonstrated that transactivation activity and motif organization among the different ZmDREB proteins were remarkably distinctive. Taken together with the diverse patterns of gene expression exhibited by these genes, it suggested that ZmDREB genes in maize may have very diversified functions.

Transgenic *Arabidopsis* plants overexpressing the ZmDREB2.7 gene were created and drought tolerance was observed to be significantly enhanced in all three independent transgenic lines. The survival rate of the vector-transformed control plants was 35%, while the survival of the ZmDREB2.7 overexpressing lines ranged from 82-97% (FIG. 3(A)-(C)). A dwarf or delayed-flowering phenotype was not observed in most of the ZmDREB2.7-OE lines, however, ZmDREB2.7-OE9 plants exhibited a slight reduction in the size of rosette leaves, which had the highest level of transgene expression (FIG. 3(A)-(C)). Unlike *Arabidopsis* DREB2A, these data support the hypothesis that post-translational regulation might not be important for ZmDREB2.7. Protein sequence analysis indicated that ZmDREB2.7 did not contain the amino acid sequence homologous to the negative regulation domain (NRD) present in *Arabidopsis* DREB2A. Taken together, these data clearly demonstrate that ZmDREB2.7 can specifically bind DRE sequences and overexpression of this gene can confer drought stress tolerance on transgenic *Arabidopsis*.

REFERENCES

1. Yamaguchi-Shinozaki K, Shinozaki K (2006) Transcriptional regulatory networks in cellular responses and tolerance to dehydration and cold stresses. Annu Rev Plant Biol 57: 781-803. doi: 10.1146/annurev.arplant.57.032905.105444
2. Baker S S, Wilhelm K S, Thomashow M F (1994) The 5′-region of *Arabidopsis thaliana* cor15a has cis-acting elements that confer cold-, drought- and ABA-regulated gene expression. Plant Mol Biol 24: 701-713. doi: 10.1007/bf00029852
3. Yamaguchi-Shinozaki K, Shinozaki K (1994) A novel cis-acting element in an *Arabidopsis* gene is involved in responsiveness to drought, low-temperature, or high-salt stress. Plant Cell 6: 251-264. doi: 10.2307/3869643
4. Jiang C, Iu B, Singh J (1996) Requirement of a CCGAC cis-acting element for cold induction of the BN115 gene from winter *Brassica napus*. Plant Mol Biol 30: 679-684. doi: 10.1007/bf00049344
5. Stockinger E J, Gilmour S J, Thomashow M F (1997) *Arabidopsis thaliana* CBF1 encodes an AP2 domain-containing transcriptional activator that binds to the C-repeat/DRE, a cis-acting DNA regulatory element that stimulates transcription in response to low temperature and water deficit. Proc Natl Acad Sci USA 94: 1035-1040. doi: 10.1073/pnas.94.3.1035
6. Liu Q, Kasuga M, Sakuma Y, Abe H, Miura S, et al. (1998) Two transcription factors, DREB1 and DREB2, with an EREBP/AP2 DNA binding domain separate two cellular signal transduction pathways in drought- and low-temperature-responsive gene expression, respectively, in *Arabidopsis*. Plant Cell 10: 1391-1406. doi: 10.2307/3870648
7. Sakuma Y, Liu Q, Dubouzet J G, Abe H, Shinozaki K, et al. (2002) DNA-binding specificity of the ERF/AP2 domain of *Arabidopsis* DREBs, transcription factors involved in dehydration- and cold-inducible gene expression. Biochem Biophys Res Commun 290: 998-1009. doi: 10.1006/bbrc.2001.6299
8. Kasuga M, Liu Q, Miura S, Yamaguchi-Shinozaki K, Shinozaki K (1999) Improving plant drought, salt, and freezing tolerance by gene transfer of a single stress-inducible transcription factor. Nat Biotechnol 17: 287-291. doi: 10.1002/9780470515778.ch13
9. Sakuma Y, Maruyama K, Osakabe Y, Qin F, Seki M, et al. (2006) Functional analysis of an *Arabidopsis* transcrip- 10. Sakuma Y, Maruyama K, Qin F, Osakabe Y, Shinozaki K, et al. (2006) Dual function of an *Arabidopsis* transcription factor DREB2A in water-stress-responsive and heat-stress-responsive gene expression. Proc Natl Acad Sci USA 103: 18822-18827. doi: 10.1073/pnas.0605639103
11. Qin F, Sakuma Y, Tran L S, Maruyama K, Kidokoro S, et al. (2008) *Arabidopsis* DREB2A-interacting proteins function as RING E3 ligases and negatively regulate plant drought stress-responsive gene expression. Plant Cell 20: 1693-1707. doi: 10.1105/tpc.107.057380
12. Haake V, Cook D, Riechmann J L, Pineda O, Thomashow M F, et al. (2002) Transcription factor CBF4 is a regulator of drought adaptation in *Arabidopsis*. Plant Physiol 130: 639-648. doi: 10.1104/pp. 006478
13. Novillo F, Alonso J M, Ecker J R, Salinas J (2004) CBF2/DREB1C is a negative regulator of CBF1/DREB1B and CBF3/DREB1A expression and plays a central role in stress tolerance in *Arabidopsis*. Proc Natl Acad Sci USA 101: 3985-3990. doi: 10.1073/pnas.0303029101
14. Lim C J, Hwang J E, Chen H, Hong J K, Yang K A, et al. (2007) Over-expression of the *Arabidopsis* DRE/CRT-binding transcription factor DREB2C enhances thermotolerance. Biochem Biophys Res Commun 362: 431-436. doi: 10.1016/j.bbrc.2007.08.007
15. Agarwal P K, Agarwal P, Reddy M K, Sopory S K (2006) Role of DREB transcription factors in abiotic and biotic stress tolerance in plants. Plant Cell Rep 25: 1263-1274. doi: 10.1007/s00299-006-0204-8
16. Mizoi J, Shinozaki K, Yamaguchi-Shinozaki K (2012) AP2/ERF family transcription factors in plant abiotic stress responses. Biochim Biophys Acta 1819: 86-96. doi: 10.1016/j.bbagrm.2011.08.004
17. Qin F, Sakuma Y, Li J, Liu Q, Li Y Q, et al. (2004) Cloning and functional analysis of a novel DREB1/CBF transcription factor involved in cold-responsive gene expression in *Zea mays* L. Plant Cell Physiol 45: 1042-1052. doi: 10.1093/pcp/pch118
18. Qin F, Kakimoto M, Sakuma Y, Maruyama K, Osakabe Y, et al. (2007) Regulation and functional analysis of ZmDREB2A in response to drought and heat stresses in *Zea mays* L. Plant J 50: 54-69. doi: 10.1111/j.1365-313x.2007.03034.x
19. Matsukura S, Mizoi J, Yoshida T, Todaka D, Ito Y, et al. (2010) Comprehensive analysis of rice DREB2-type genes that encode transcription factors involved in the expression of abiotic stress-responsive genes. Mol Genet Genomics 283: 185-196. doi: 10.1007/s00438-009-0506-y
20. Egawa C, Kobayashi F, Ishibashi M, Nakamura T, Nakamura C, et al. (2006) Differential regulation of transcript accumulation and alternative splicing of a DREB2 homolog under abiotic stress conditions in common wheat. Genes Genet Syst 81: 77-91. doi: 10.1266/ggs.81.77
21. Xue G P, Loveridge C W (2004) HvDRF1 is involved in abscisic acid-mediated gene regulation in barley and produces two forms of AP2 transcriptional activators, interacting preferably with a CT-rich element. Plant J 37: 326-339. doi: 10.1046/j.1365-313x.2003.01963.x
22. Mao D, Chen C (2012) Colinearity and similar expression pattern of rice DREB1s reveal their functional conservation in the cold-responsive pathway. PLoS One 7: e47275.

```
Sequence listing
ZmDREB2.7 nucleic acid sequence (cDNA)
                                                                              SEQ ID NO. 1
acacacagtcacagcacacgcagccaccgaggactgcattgctagcatccatcgccatca gtcgccatatcgatctgcgcacgaagctagtagtccagatggatcgggtgccgccgccgg tctccatgcaggtggctgcgatgcagcgacatcagcagcagcagcagttcgtccaccacc tgcagcaggtccaccagcaaggtacgcagcacgagcaaccgccgccaccgcaccagaacg gcagcagcagcagcggcaggaccggcggcggccgcaagtgctgcccgctgcggcggtcgc gcaaggggtgcatgaagggcaagggcgggccggacaaccagcagtgcccctttccgcggcg tccggcagcgcacctggggcaagtgggtggccgagatccgcgagcccaaccgcggcgcgc gcctctggctcggcaccttcggcagcgcgctcgaggccgcgcgcgcctacgacgccgcgg ccaggacgctctacggcgactgcgctcgcctaaacctgcagctagtgcctccgtcggcgg ctgcggcagccgccggaggaggaggaccggcggtcgtcgcgtctccgtccctgacaccg tggctggccctgctgctgctgctggtggtggtggacacaactgccatcaccagtacctgc agcagcagcacgccatggcggcgcctatgatgatgatgcactcctcctgctgctccgccg acgggtcgtcgtcaaactccgattccatttccaactcctgctcgtcaccggtgaccacgg cggcctcgccagcctacagccaccaccagacgatgttccagacacctgcactgcagccgt catgcggcgcaatgacgatggcggccgctgcgccgcatgtgcagggcttccacgtcggcg acgacgacactaccaccgcgatggcgatgcaccgtcatcagcagatgatgcgcgagctgg cggaggcgcctctgcaccaggaggcagacgacttcgaggacttcgtgacgcggctgccca aggcggaggacttcggcctgcagggcttccaggaggtggcccccgaggtgttcgacgacg
```

-continued

```
ccgccggcatctgggaccacgcggccgcctgggagcccccaccatgatgatcgactctg
gcgcccagccccagcagcagctcgtcgtccctctttgactcgctcgtcgatgacgccgcg
cgccctgcaccagctactgcttcgttcccagctgcatcgaactggccggtgtacgtggcg
gagtgatacgacgcgcgcgctatgcatgacaccactgcacaggtggttcttgcatgtgtt
gcttacgcctcgagacgtacgtacataataccagtatgtatgtaccggatggttactctg
atatgactgtatttctcctagttattcgtgggtttcatttggataatgtttcaggttttg
taaaatatatactttagtagtagtggtgtcttaaatatatgctcctagctatatatctag
tctctgtgtggtatatgcatggccgctagttagcttgtacaatattaccatatatagata
tattaatttcgcttttactaaata
```

ZmDREB2.7 nucleic acid sequence (coding sequence)

SEQ ID NO. 2

```
atggatcgggtgccgccgccggtctccatgcaggtggctgcgatgcagcgacatcagcagcagcagcagttc
gtccaccacctgcagcaggtccaccagcaaggtacgcagcacgagcaaccgccgccaccgcaccagaacg
gcagcagcagcagcggcaggaccggcggcggccgcaagtgctgcccgctgcggcggtcgc
gcaagggggtgcatgaagggcaagggcgggccggacaaccagcagtgccccttccgcggcg
tccggcagcgcacctggggcaagtgggtggccgagatccgcgagcccaaccgcggcgcgc
gcctctggctcggcaccttcggcagcgcgctcgaggccgcgcgcgcctacgacgccgcgg
ccaggacgctctacggcgactgcgctcgcctaaacctgcagctagtgcctccgtcggcgg
ctgcggcagccgccggaggaggaggaccggcggtcgtcgcgtctccgtcccctgacaccg
tggctggccctgctgctgctgctggtggtggtggacacaactgccatcaccagtacctgc
agcagcagcacgccatggcggcgcctatgatgatgatgcactcctcctgctgctccgccg
acgggtcgtcgtcaaactccgattccatttccaactcctgctcgtcaccggtgaccacgg
cggcctcgccagcctacagccaccaccagacgatgttccagacacctgcactgcagccgt
catgcggcgcaatgacgatggcggccgctgcgccgcatgtgcagggcttccacgtcggcg
acgacgacactaccaccgcgatggcgatgcaccgtcatcagcagatgatgcgcgagctgg
cggaggcgcctctgcaccaggaggcagacgacttcgaggacttcgtgacgcggctgccca
aggcggaggacttcggcctgcagggcttccaggaggtggcccccgaggtgttcgacgacg
ccgccggcatctgggaccacgcggccgcctgggagcccccaccatgatgatcgactctg
gcgcccagccccagcagcagctcgtcgtccctctttga
```

ZmDREB2.7 amino acid sequence

SEQ ID NO. 3

```
Met Asp Arg Val Pro Pro Pro Val Ser Met Gln Val Ala Ala Met Gln Arg His Gln Gln Gln
Gln Gln Phe Val His His Leu Gln Gln Val His Gln Gln Gly Thr Gln His Glu Gln Pro Pro Pro
Pro His Gln Asn Gly Ser Ser Ser Ser Gly Arg Thr Gly Gly Gly Arg Lys Cys Cys Pro Leu Arg
Arg Ser Arg Lys Gly Cys Met Lys Gly Lys Gly Gly Pro Asp Asn Gln Gln Cys Pro Phe Arg
Gly Val Arg Gln Arg Thr Trp Gly Lys Trp Val Ala Glu Ile Arg Glu Pro Asn Arg Gly Ala Arg
Leu Trp Leu Gly Thr Phe Gly Ser Ala Leu Glu Ala Ala Arg Ala Tyr Asp Ala Ala Ala Arg Thr
Leu Tyr Gly Asp Cys Ala Arg Leu Asn Leu Gln Leu Val Pro Pro Ser Ala Ala Ala Ala Ala
Gly Gly Gly Gly Pro Ala Val Val Ala Ser Pro Ser Pro Asp Thr Val Ala Gly Pro Ala Ala Ala
Ala Gly Gly Gly Gly His Asn Cys His His Gln Tyr Leu Gln Gln Gln His Ala Met Ala Ala Pro
Met Met Met Met His Ser Ser Cys Cys Ser Ala Asp
Gly Ser Ser Ser Asn Ser Asp Ser Ile Ser Asn Ser Cys Ser Ser Pro Val Thr Thr Ala Ala Ser
```

-continued

Pro Ala Tyr Ser His His Gln Thr Met Phe Gln Thr Pro Ala Leu Gln Pro Ser Cys Gly Ala Met

Thr Met Ala Ala Ala Ala Pro His Val Gln Gly Phe His Val Gly Asp Asp Thr Thr Ala

Met Ala Met His Arg His Gln Gln Met Met Arg Glu Leu Ala Glu Ala Pro Leu His Gln Glu Ala

Asp Asp Phe Glu Asp Phe Val Thr Arg Leu Pro Lys Ala Glu Asp Phe Gly Leu Gln Gly Phe

Gln Glu Val Ala Pro Glu Val Phe Asp Asp Ala Ala Gly Ile Trp Asp His Ala Ala Trp Glu

Pro Pro Thr Met Met Ile Asp Ser Gly Ala Gln Pro Gln Gln Leu Val Val Pro Leu

ZmDREB2.7 promoter sequence from the drought tolerant inbred line
CIMBL70.

SEQ ID NO. 4

GGCTCGCGGA TCGGCGCAGT CCATGGATAG ATGGAGATGG ATCCATCCAT

GGATAGATCA

TAGATAGATA GATAGGCAGC CCATGGCCGT GGCTGCATCT GCGGGCTGGG

CGGGCTGCAT

CAGCGTGACG CCGTGACCTC ACCCTGGTTC GGTCGCCCCC CGGCCGCCAC

GTGGCCCAGC

GGCCACGACG TGGACCCCAC AGGGGCTTCC ATGTGTCAAG CCCCGCTGGC

CCCCACCACT

TCGTGTCACC CGCCTCCTTC ACTTGGCGTG CCGCACCCCC ACGCGTGGCC

CCACGCCCAG

GCCCCGCCTC CCTACACGGA GGCGTCATGC AGTGCCATGC GCCGGCTTCC

CCCCTGCCCC

CTCCGTCCGC CCGCCTTCAT TCAGCTTCCG GCTTCCGCTG TTCCGCACAC

CACCGAAAAC

TGGTGCACGG CCTGCAGTGC AGTGCATGCC ATGCCAGCTG CCTATATATA

CCAGGCCAGG

GAGCGGGAGC CTCACACACA GTCACAGACT CACAGCACAC GCAGCCACCG

AGGACTGCAT

TGCTAGCATC GTCCATCGCC ATCAGTCGCC ATATCTCGAT CTGC

---

What is claimed is:

1. A transgenic plant expressing a nucleic acid construct comprising a nucleic acid encoding SEQ ID NO: 3 or a polypeptide having at least 95% identity to SEQ ID NO: 3, wherein said plant exhibits increased drought resistance compared to a plant not comprising said nucleic acid molecule.

2. A plant according to claim 1 wherein said nucleic acid sequence encodes a polypeptide having at least 98% identity to SEQ ID NO: 3.

3. A plant according to claim 1 wherein said polypeptide comprises SEQ ID No: 16, 19, 21, and 24 or a sequence having at least 95% identity thereto, and comprises SEQ ID NO: 17, 18, 19, 20, 22 and 23 or a sequence having at least 98% identity thereto.

4. A plant according to claim 1 wherein said construct further comprises a regulatory sequence.

5. A plant according to claim 4, wherein said regulatory sequence is a stress inducible promoter.

6. A plant according to claim 4, wherein said regulatory sequence comprises SEQ ID NO. 4.

7. A plant according to claim 1, wherein said plant is a monocot or dicot plant.

8. A plant according to claim 7 wherein said plant is a crop plant or biofuel plant.

9. A plant according to claim 8 wherein said crop plant is selected from maize, rice, wheat, oilseed rape, sorghum, soybean, potato, tomato, grape, barley, pea, bean, field bean, lettuce, cotton, sugar cane, sugar beet, broccoli or other vegetable brassicas or poplar.

10. A plant according to claim 9 wherein said crop plant is maize.

11. A plant according to claim 9 wherein said plant has increased drought resistance.

12. A product derived from a plant as defined in claim 9 or from a part thereof wherein said product comprises said nucleic acid.

13. A vector comprising a nucleic acid encoding SEQ ID NO: 3 or a polypeptide having at least 95% identity to SEQ ID NO: 3 operably linked to a stress-inducible promoter.

14. A vector according to claim 13 wherein said vector is an expression vector.

15. A vector according to claim 13 wherein said regulatory sequence is SEQ ID NO. 4.

16. A host cell comprising a vector according to claim 13.

17. A host cell according to claim 16 wherein said host cell is a bacterial or a plant cell.

18. A method of increasing stress resistance in a plant, the method comprising mutating the genome of said plant such that said plant has increased expression of a nucleic acid encoding SEQ ID NO: 3 or a polypeptide having at least 95% identity to SEQ ID NO: 3.

19. The method of claim 18 wherein said stress is moderate.

20. A method for increasing yield or drought resistance of a plant said method comprising introducing and expressing in said plant a nucleic acid construct comprising nucleic acid encoding SEQ ID NO: 3 or a polypeptide having at last 95% identity to SEQ ID NO: 3.

21. A method according to claim 20 wherein said nucleic acid sequence encodes a polypeptide having at least 98% identity to SEQ ID NO: 3.

22. A method according to claim 20 wherein wherein said polypeptide comprises SEQ ID No: 16, 19, 21, and 24 or a sequence having at least 95% identity thereto, and comprises SEQ ID NO: 17, 18, 19, 20, 22 and 23 or a sequence having at least 98% identity thereto.

23. A method according to claim 20 wherein said construct further comprises a regulatory sequence.

24. A method according to claim 23 wherein said regulatory sequence is a stress inducible promoter.

25. A method according to claim 23 wherein said regulatory sequence is SEQ ID NO. 4.

26. A method according to claim 20 wherein said plant is a monocot or dicot plant.

27. A method according to claim 26 wherein said plant is a crop plant or biofuel plant.

28. A method according to claim 27 wherein said crop plant is selected from maize, rice, wheat, oilseed rape, sorghum, soybean, potato, tomato, grape, barley, pea, bean, field bean, lettuce, cotton, sugar cane, sugar beet, broccoli or other vegetable brassicas or poplar.

29. A method according to claim 27 wherein said crop plant is maize.

30. A method according to claim 20, wherein said stress is moderate or severe stress.

31. The plant of claim 1, wherein said nucleic acid is selected from SEQ ID NO: 1 or 2 or a sequence having at least 95% identity thereto.

32. The plant of claim 1, wherein said construct further comprises the regulatory sequence of SEQ ID NO: 4 or a functional fragment thereof.

33. The vector of claim 13, wherein said nucleic acid encodes a polypeptide having at least 98% identity to SEQ ID NO: 3.

34. The vector of claim 13, wherein said polypeptide comprises SEQ ID NO: 16, 19, 21, and 24 or a sequence having at least 95% identity thereto, and comprises SEQ ID NO: 17, 18, 19, 20, 22 and 23 or a sequence having at least 98% identity thereto.

35. The vector of claim 13, wherein said nucleic acid is selected from SEQ ID NO: 1 or 2 or a sequence having at least 95% identity thereto.

36. The vector of claim 13, wherein said vector further comprises a regulatory sequence of SEQ ID NO: 4 or a functional fragment thereof.

37. The method of claim 20, wherein said nucleic acid is operably linked to a regulatory region comprising SEQ ID NO: 4 or a functional fragment thereof.

* * * * *

SEQUENCE LISTING

<160> NUMBER OF SEQ ID NOS: 24

<210> SEQ ID NO 1
<211> LENGTH: 1584
<212> TYPE: DNA
<213> ORGANISM: Zea mays

<400> SEQUENCE: 1
acacacagtc acagcacacg cagccaccga ggactgcatt gctagcatcc atcgccatca      60
gtcgccatat cgatctgcgc acgaagctag tagtccagat ggatcgggtg ccgccgccgg     120
tctccatgca ggtggctgcg atgcagcgac atcagcagca gcagcagttc gtccaccacc     180
tgcagcaggt ccaccagcaa ggtacgcagc acgagcaacc gccgccaccg caccagaacg     240
gcagcagcag cagcggcagg accggcggcg gccgcaagtg ctgcccgctg cggcggtcgc     300
gcaaggggtg catgaagggc aagggcgggc cggacaacca gcagtgcccc ttccgcggcg     360
tccggcagcg cacctggggc aagtgggtgg ccgagatccg cgagcccaac cgcggcgcgc     420

| | | | |
|---|---|---|---|
| gcctctggct | cggcaccttc | ggcagcgcgc | tcgaggccgc gcgcgcctac gacgccgcgg | 480 |
| ccaggacgct | ctacggcgac | tgcgctcgcc | taaacctgca gctagtgcct ccgtcggcgg | 540 |
| ctgcggcagc | cgccggagga | ggaggaccgg | cggtcgtcgc gtctccgtcc cctgacaccg | 600 |
| tggctggccc | tgctgctgct | gctggtggtg | gtggacacaa ctgccatcac cagtacctgc | 660 |
| agcagcagca | cgccatggcg | cgcctatga  | tgatgatgca ctcctcctgc tgctccgccg | 720 |
| acgggtcgtc | gtcaaactcc | gattccattt | ccaactcctg ctcgtcaccg gtgaccacgg | 780 |
| cggcctcgcc | agcctacagc | caccaccaga | cgatgttcca gacacctgca ctgcagccgt | 840 |
| catgcggcgc | aatgacgatg | gcggccgctg | cgccgcatgt gcagggcttc cacgtcggcg | 900 |
| acgacgacac | taccaccgcg | atggcgatgc | accgtcatca gcagatgatg cgcgagctgg | 960 |
| cggaggcgcc | tctgcaccag | gaggcagacg | acttcgagga cttcgtgacg cggctgccca | 1020 |
| aggcggagga | cttcggcctg | cagggcttcc | aggaggtggc ccccgaggtg ttcgacgacg | 1080 |
| ccgccggcat | ctgggaccac | gcggccgcct | gggagccccc caccatgatg atcgactctg | 1140 |
| gcgcccagcc | ccagcagcag | ctcgtcgtcc | ctctttgact cgctcgtcga tgacgccgcg | 1200 |
| cgccctgcac | cagctactgc | ttcgttccca | gctgcatcga actggccggt gtacgtggcg | 1260 |
| gagtgatacg | acgcgcgcgc | tatgcatgac | accactgcac aggtggttct tgcatgtgtt | 1320 |
| gcttacgcct | cgagacgtac | gtacataata | ccagtatgta tgtaccggat ggttactctg | 1380 |
| atatgactgt | atttctccta | gttattcgtg | ggtttcattt ggataatgtt tcaggttttg | 1440 |
| taaaatatat | actttagtag | tagtggtgtc | ttaaatatat gctcctagct atatatctag | 1500 |
| tctctgtgtg | gtatatgcat | ggccgctagt | tagcttgtac aatattacca tatatagata | 1560 |
| tattaatttc | gcttttacta | aata       | | 1584 |

<210> SEQ ID NO 2
<211> LENGTH: 1080
<212> TYPE: DNA
<213> ORGANISM: Zea mays

<400> SEQUENCE: 2

| | | | |
|---|---|---|---|
| atggatcggg | tgccgccgcc | ggtctccatg | caggtggctg cgatgcagcg acatcagcag | 60 |
| cagcagcagt | tcgtccacca | cctgcagcag | gtccaccagc aaggtacgca gcacgagcaa | 120 |
| ccgccgccac | cgcaccagaa | cggcagcagc | agcagcggca ggaccggcgg cggccgcaag | 180 |
| tgctgcccgc | tgcggcggtc | gcgcaagggg | tgcatgaagg gcaagggcgg gccggacaac | 240 |
| cagcagtgcc | ccttccgcgg | cgtccggcag | cgcacctggg gcaagtgggt ggccgagatc | 300 |
| cgcgagccca | accgcggcgc | gcgcctctgg | ctcggcacct tcggcagcgc gctcgaggcc | 360 |
| gcgcgcgcct | acgacgccgc | ggccaggacg | ctctacggcg actgcgctcg cctaaacctg | 420 |
| cagctagtgc | ctccgtcggc | ggctgcggca | gccgccggag gaggaggacc ggcggtcgtc | 480 |
| gcgtctccgt | cccctgacac | cgtggctggc | cctgctgctg ctgctggtgg tggtggacac | 540 |
| aactgccatc | accagtacct | gcagcagcag | cacgccatgg cggcgcctat gatgatgatg | 600 |
| cactcctcct | gctgctccgc | cgacgggtcg | tcgtcaaact ccgattccat ttccaactcc | 660 |
| tgctcgtcac | cggtgaccac | ggcggcctcg | ccagcctaca gccaccacca gacgatgttc | 720 |
| cagacacctg | cactgcagcc | gtcatgcggc | gcaatgacga tggcggccgc tgcgccgcat | 780 |
| gtgcagggct | tccacgtcgg | cgacgacgac | actaccaccg cgatggcgat gcaccgtcat | 840 |
| cagcagatga | tgcgcgagct | ggcggaggcg | cctctgcacc aggaggcaga cgacttcgag | 900 |

-continued

```
gacttcgtga cgcggctgcc caaggcggag gacttcggcc tgcagggctt ccaggaggtg    960
gcccccgagg tgttcgacga cgccgccggc atctgggacc acgcggccgc ctgggagccc   1020
cccaccatga tgatcgactc tggcgcccag ccccagcagc agctcgtcgt ccctctttga   1080
```

<210> SEQ ID NO 3
<211> LENGTH: 359
<212> TYPE: PRT
<213> ORGANISM: Zea mayes

<400> SEQUENCE: 3

```
Met Asp Arg Val Pro Pro Val Ser Met Gln Val Ala Ala Met Gln
1               5                   10                  15

Arg His Gln Gln Gln Gln Phe Val His His Leu Gln Gln Val His
                20                  25                  30

Gln Gln Gly Thr Gln His Glu Gln Pro Pro Pro His Gln Asn Gly
                35                  40                  45

Ser Ser Ser Gly Arg Thr Gly Gly Gly Arg Lys Cys Cys Pro Leu
50                  55                  60

Arg Arg Ser Arg Lys Gly Cys Met Lys Gly Lys Gly Gly Pro Asp Asn
65                  70                  75                  80

Gln Gln Cys Pro Phe Arg Gly Val Arg Gln Arg Thr Trp Gly Lys Trp
                85                  90                  95

Val Ala Glu Ile Arg Glu Pro Asn Arg Gly Ala Arg Leu Trp Leu Gly
                100                 105                 110

Thr Phe Gly Ser Ala Leu Glu Ala Ala Arg Ala Tyr Asp Ala Ala Ala
                115                 120                 125

Arg Thr Leu Tyr Gly Asp Cys Ala Arg Leu Asn Leu Gln Leu Val Pro
130                 135                 140

Pro Ser Ala Ala Ala Ala Ala Gly Gly Gly Pro Ala Val Val
145                 150                 155                 160

Ala Ser Pro Ser Pro Asp Thr Val Ala Gly Pro Ala Ala Ala Gly
                165                 170                 175

Gly Gly Gly His Asn Cys His His Gln Tyr Leu Gln Gln Gln His Ala
                180                 185                 190

Met Ala Ala Pro Met Met Met His Ser Ser Cys Cys Ser Ala Asp
                195                 200                 205

Gly Ser Ser Ser Asn Ser Asp Ser Ile Ser Asn Ser Cys Ser Ser Pro
                210                 215                 220

Val Thr Thr Ala Ala Ser Pro Ala Tyr Ser His His Gln Thr Met Phe
225                 230                 235                 240

Gln Thr Pro Ala Leu Gln Pro Ser Cys Gly Ala Met Thr Met Ala Ala
                245                 250                 255

Ala Ala Pro His Val Gln Gly Phe His Val Gly Asp Asp Thr Thr
                260                 265                 270

Thr Ala Met Ala Met His Arg His Gln Gln Met Met Arg Glu Leu Ala
                275                 280                 285

Glu Ala Pro Leu His Gln Glu Ala Asp Asp Phe Glu Asp Phe Val Thr
                290                 295                 300

Arg Leu Pro Lys Ala Glu Asp Phe Gly Leu Gln Gly Phe Gln Glu Val
305                 310                 315                 320

Ala Pro Glu Val Phe Asp Asp Ala Ala Gly Ile Trp Asp His Ala Ala
                325                 330                 335

Ala Trp Glu Pro Pro Thr Met Met Ile Asp Ser Gly Ala Gln Pro Gln
                340                 345                 350
```

Gln Gln Leu Val Val Pro Leu
        355

<210> SEQ ID NO 4
<211> LENGTH: 584
<212> TYPE: DNA
<213> ORGANISM: Zea mayes

<400> SEQUENCE: 4

```
ggctcgcgga tcggcgcagt ccatggatag atggagatgg atccatccat ggatagatca      60
tagatagata gataggcagc ccatggccgt ggctgcatct gcgggctggg cgggctgcat     120
cagcgtgacg ccgtgacctc acctggttc ggtcgcccc cggccgccac gtggcccagc      180
ggccacgacg tggaccccac aggggcttcc atgtgtcaag ccccgctggc ccccaccact     240
tcgtgtcacc cgcctccttc acttggcgtg ccgcacccc acgcgtggcc ccacgcccag      300
gccccgcctc cctacacgga ggcgtcatgc agtgccatgc gccggcttcc cccctgcccc     360
ctccgtccgc ccgccttcat tcagcttccg gcttccgctg ttccgcacac caccgaaaac     420
tggtgcacgg cctgcagtgc agtgcatgcc atgccagctg cctatatata ccaggccagg     480
gagcgggagc ctcacacaca gtcacagact cacagcacac gcagccaccg aggactgcat     540
tgctagcatc gtccatcgcc atcagtcgcc atatctcgat ctgc                      584
```

<210> SEQ ID NO 5
<211> LENGTH: 5
<212> TYPE: PRT
<213> ORGANISM: Artificial Sequence
<220> FEATURE:
<223> OTHER INFORMATION: Primer

<400> SEQUENCE: 5

Arg Arg Arg Arg Arg
1               5

<210> SEQ ID NO 6
<211> LENGTH: 6
<212> TYPE: PRT
<213> ORGANISM: Artificial Sequence
<220> FEATURE:
<223> OTHER INFORMATION: Primer

<400> SEQUENCE: 6

His His His His His His
1               5

<210> SEQ ID NO 7
<211> LENGTH: 8
<212> TYPE: PRT
<213> ORGANISM: Artificial Sequence
<220> FEATURE:
<223> OTHER INFORMATION: Primer

<400> SEQUENCE: 7

Asp Tyr Lys Asp Asp Asp Asp Lys
1               5

<210> SEQ ID NO 8
<211> LENGTH: 8
<212> TYPE: PRT
<213> ORGANISM: Artificial Sequence
<220> FEATURE:
<223> OTHER INFORMATION: Primer

```
<400> SEQUENCE: 8

Trp Ser His Pro Gln Phe Glu Lys
1               5

<210> SEQ ID NO 9
<211> LENGTH: 10
<212> TYPE: PRT
<213> ORGANISM: Artificial Sequence
<220> FEATURE:
<223> OTHER INFORMATION: Primer

<400> SEQUENCE: 9

Glu Gln Lys Leu Ile Ser Glu Glu Asp Leu
1               5                   10

<210> SEQ ID NO 10
<211> LENGTH: 19
<212> TYPE: DNA
<213> ORGANISM: Artificial Sequence
<220> FEATURE:
<223> OTHER INFORMATION: Primer

<400> SEQUENCE: 10
tatgatgatg atgcactcc                                               19

<210> SEQ ID NO 11
<211> LENGTH: 18
<212> TYPE: DNA
<213> ORGANISM: Artificial Sequence
<220> FEATURE:
<223> OTHER INFORMATION: Primer

<400> SEQUENCE: 11
gagttggaaa tggaatcg                                                18

<210> SEQ ID NO 12
<211> LENGTH: 23
<212> TYPE: DNA
<213> ORGANISM: Artificial Sequence
<220> FEATURE:
<223> OTHER INFORMATION: Primer

<400> SEQUENCE: 12
ggtaacattg tgctcagtgg tgg                                          23

<210> SEQ ID NO 13
<211> LENGTH: 22
<212> TYPE: DNA
<213> ORGANISM: Artificial Sequence
<220> FEATURE:
<223> OTHER INFORMATION: GCATCAATTCGATCACTCAGAG

<400> SEQUENCE: 13
gcatcaattc gatcactcag ag                                           22

<210> SEQ ID NO 14
<211> LENGTH: 18
<212> TYPE: DNA
<213> ORGANISM: Artificial Sequence
<220> FEATURE:
<223> OTHER INFORMATION: Primer

<400> SEQUENCE: 14
atggatcggg tgccgccg                                                18
```

```
<210> SEQ ID NO 15
<211> LENGTH: 19
<212> TYPE: DNA
<213> ORGANISM: Artificial Sequence
<220> FEATURE:
<223> OTHER INFORMATION: Primer

<400> SEQUENCE: 15
tcaaagaggg acgacgagc                                                   19

<210> SEQ ID NO 16
<211> LENGTH: 22
<212> TYPE: PRT
<213> ORGANISM: Artificial Sequence
<220> FEATURE:
<223> OTHER INFORMATION: Primer

<400> SEQUENCE: 16

Gln Gln Gln Gln Gln Phe Val His His Leu Gln Gln Val His Gln Gln
1               5                   10                  15

Gly Thr Gln His Glu Gln
            20

<210> SEQ ID NO 17
<211> LENGTH: 8
<212> TYPE: PRT
<213> ORGANISM: Artificial Sequence
<220> FEATURE:
<223> OTHER INFORMATION: Primer

<400> SEQUENCE: 17

Gly Arg Lys Cys Cys Pro Leu Arg
1               5

<210> SEQ ID NO 18
<211> LENGTH: 8
<212> TYPE: PRT
<213> ORGANISM: Artificial Sequence
<220> FEATURE:
<223> OTHER INFORMATION: Primer

<400> SEQUENCE: 18

Arg Ser Arg Lys Gly Cys Met Lys
1               5

<210> SEQ ID NO 19
<211> LENGTH: 11
<212> TYPE: PRT
<213> ORGANISM: Artificial Sequence
<220> FEATURE:
<223> OTHER INFORMATION: Primer

<400> SEQUENCE: 19

His Asn Cys His His Gln Tyr Leu Gln Gln Gln
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Primer

<400> SEQUENCE: 20

His Asn Cys His His Gln Tyr Leu Gln Gln Gln
1               5                   10
```

```
<210> SEQ ID NO 21
<211> LENGTH: 28
<212> TYPE: PRT
<213> ORGANISM: Artificial Sequence
<220> FEATURE:
<223> OTHER INFORMATION: Primer

<400> SEQUENCE: 21

Met Ala Ala Pro Met Met Met Met His Ser Ser Cys Cys Ser Ala Asp
1               5                   10                  15

Gly Ser Ser Ser Asn Ser Asp Ser Ile Ser Asn Ser
            20                  25

<210> SEQ ID NO 22
<211> LENGTH: 9
<212> TYPE: PRT
<213> ORGANISM: Artificial Sequence
<220> FEATURE:
<223> OTHER INFORMATION: Primer

<400> SEQUENCE: 22

Tyr Ser His His Gln Thr Met Phe Gln
1               5

<210> SEQ ID NO 23
<211> LENGTH: 28
<212> TYPE: PRT
<213> ORGANISM: Artificial Sequence
<220> FEATURE:
<223> OTHER INFORMATION: Primer

<400> SEQUENCE: 23

Asp Asp Asp Thr Thr Thr Ala Met Ala Met His Arg His Gln Gln Met
1               5                   10                  15

Met Arg Glu Leu Ala Glu Ala Pro Leu His Gln Glu
            20                  25

<210> SEQ ID NO 24
<211> LENGTH: 50
<212> TYPE: PRT
<213> ORGANISM: Artificial Sequence
<220> FEATURE:
<223> OTHER INFORMATION: Primer

<400> SEQUENCE: 24

Asp Asp Phe Glu Asp Phe Val Thr Arg Leu Pro Lys Ala Glu Asp Phe
1               5                   10                  15

Gly Leu Gln Gly Phe Gln Glu Val Ala Pro Glu Val Phe Asp Asp Ala
            20                  25                  30

Ala Gly Ile Trp Asp His Ala Ala Ala Trp Glu Pro Pro Thr Met Met
        35                  40                  45

Ile Asp
    50
```